United States Patent
Schatzberger

(10) Patent No.: US 7,670,333 B2
(45) Date of Patent: Mar. 2, 2010

(54) METHOD AND APPARATUS FOR POSITIONING A SURGICAL INSTRUMENT

(75) Inventor: Shaike Schatzberger, Haifa (IL)

(73) Assignee: UC-Care Ltd., Yokneam (IL)

(*) Notice: Subject to any disclaimer, the term of this patent is extended or adjusted under 35 U.S.C. 154(b) by 1294 days.

(21) Appl. No.: 10/517,768

(22) PCT Filed: Jun. 26, 2003

(86) PCT No.: PCT/IL03/00540

§ 371 (c)(1),
(2), (4) Date: Dec. 27, 2004

(87) PCT Pub. No.: WO2004/002319

PCT Pub. Date: Jan. 8, 2004

(65) Prior Publication Data

US 2005/0261707 A1 Nov. 24, 2005

Related U.S. Application Data

(60) Provisional application No. 60/391,599, filed on Jun. 27, 2002.

(51) Int. Cl.
*A61B 17/00* (2006.01)
(52) U.S. Cl. .................................. 606/1; 128/898
(58) Field of Classification Search ............ 606/1, 606/27–52; 128/898
See application file for complete search history.

(56) References Cited

U.S. PATENT DOCUMENTS

| 5,370,675 | A | 12/1994 | Edwards et al. |
| 5,480,417 | A | 1/1996 | Hascoet et al. |
| 5,540,655 | A | 7/1996 | Edwards et al. |
| 5,590,657 | A | 1/1997 | Cain et al. |
| 5,676,692 | A | 10/1997 | Sanghvi et al. |
| 5,788,692 | A * | 8/1998 | Campbell et al. ............. 606/33 |
| 5,992,419 | A | 11/1999 | Sterzer et al. |
| 6,017,361 | A | 1/2000 | Mikus et al. |
| 6,572,553 | B2 * | 6/2003 | Crowley ..................... 600/463 |
| 6,669,655 | B1 | 12/2003 | Acker et al. |
| 6,994,706 | B2 * | 2/2006 | Chornenky et al. ........... 606/41 |
| 2002/0111615 | A1 | 8/2002 | Cosman et al. |

OTHER PUBLICATIONS

IPRP CH I Jan. 22, 2009.
International Search Report dated Sep. 4, 2008 From the International Searching Authority Re.: Application No. PCT/IL06/01160.
Written Opinion Dated Sep. 4, 2008 From the International Searching Authority Re.: Application No. PCT/IL06/01160.

* cited by examiner

*Primary Examiner*—Roy D Gibson

(57) ABSTRACT

Presented are methods and apparatus for delivering a surgical instrument to a treatment site within the body of a subject, enabling accurate placement of surgical tools in areas not directly visible to a surgeon during a surgical procedure, while reducing or eliminating need for real-time imaging modalities to guide placement of those surgical tools. A treatment tool is guided to a treatment site by placing a guiding element at a reference site within a body of a subject, the reference site having a known spatial relationship to the treatment site, and utilizing a positioning tool to guide a treatment tool to a locus so positioned with respect to that guiding element that the spatial relationship between that guiding element and that locus is substantially similar to the spatial relationship known to exist between the reference site and the treatment site, thereby positioning the treatment tool substantially at the treatment site. Methods and apparatus for treatment of Benign Prostate Hyperplasia are also presented.

62 Claims, 23 Drawing Sheets

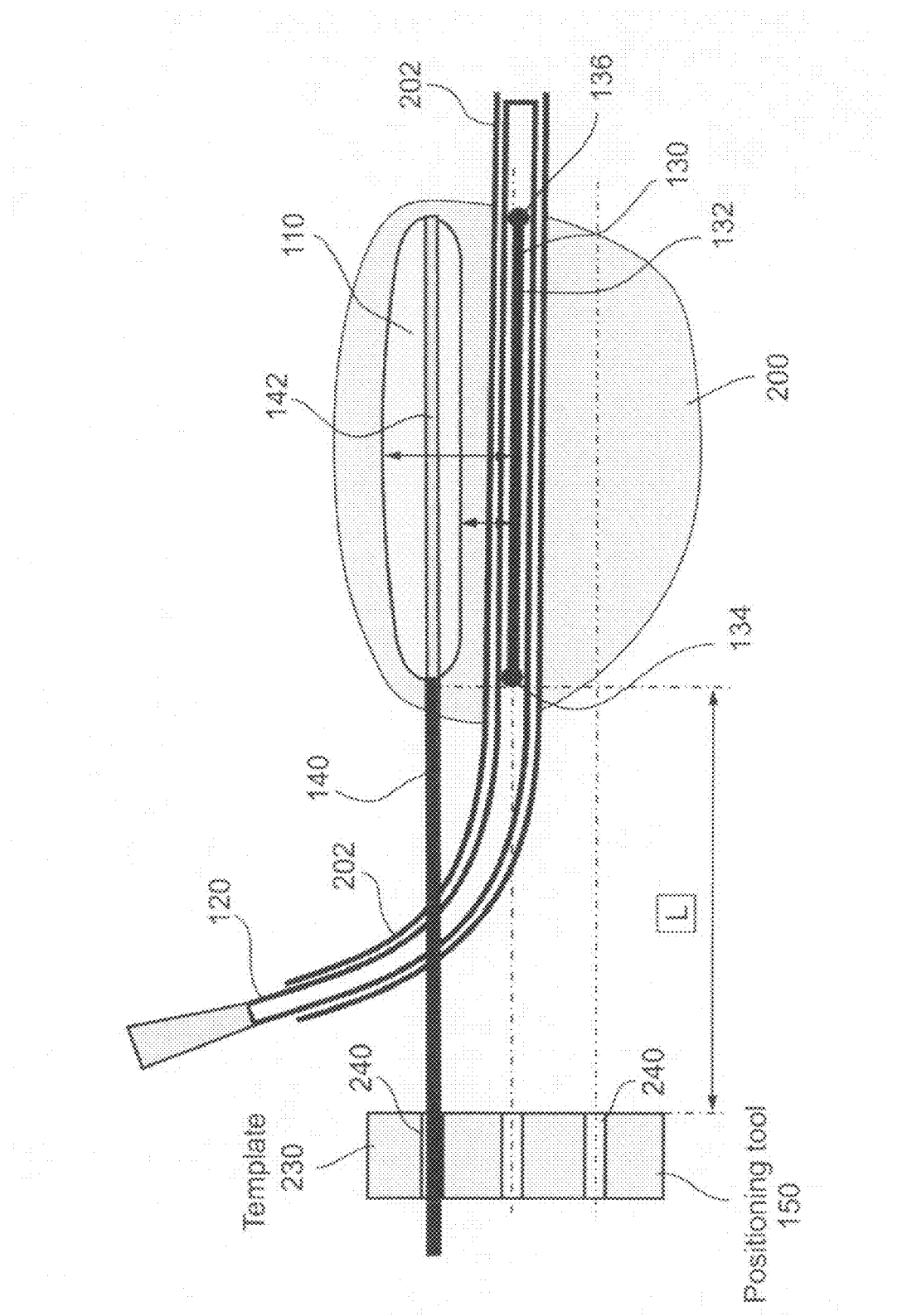

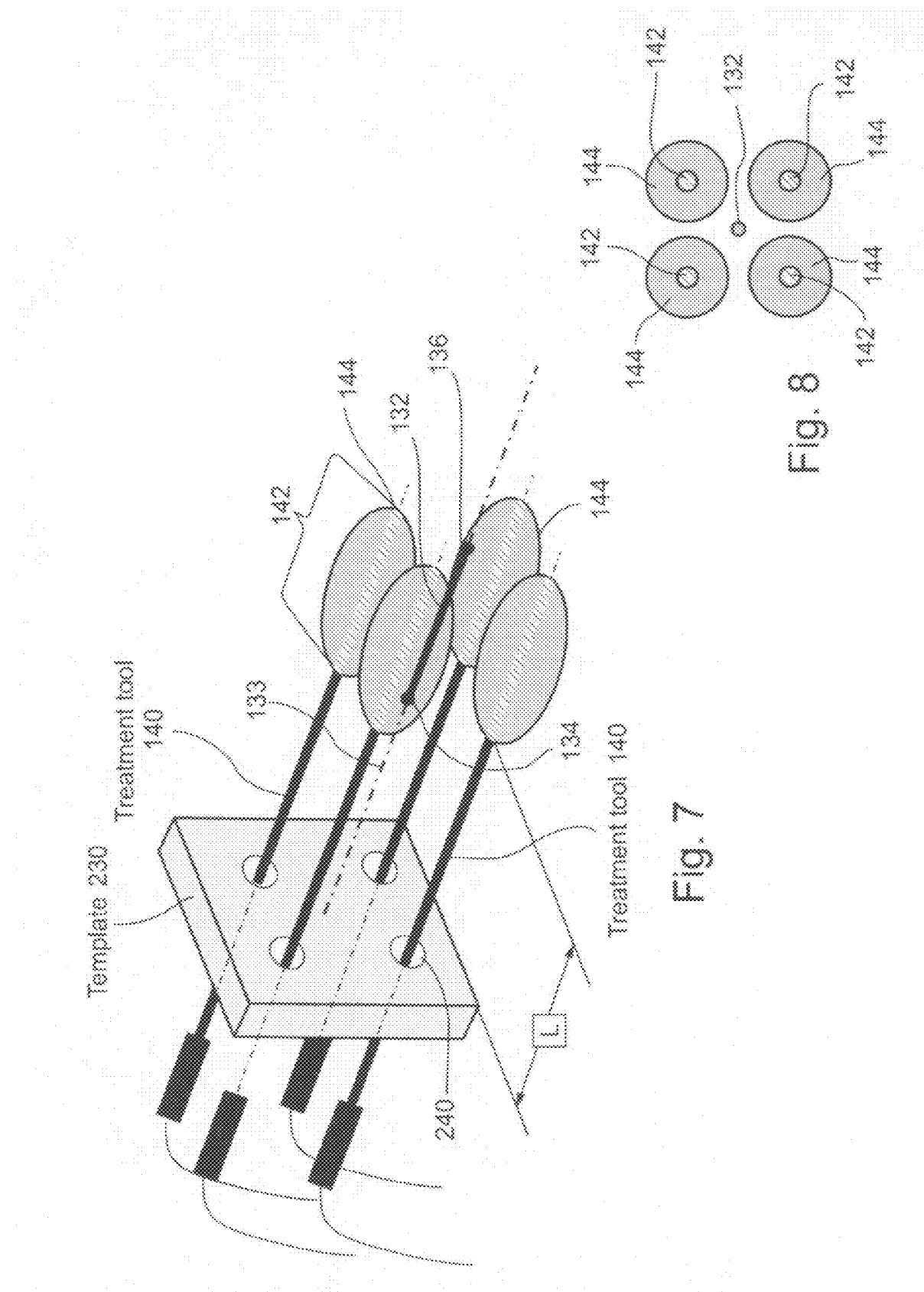

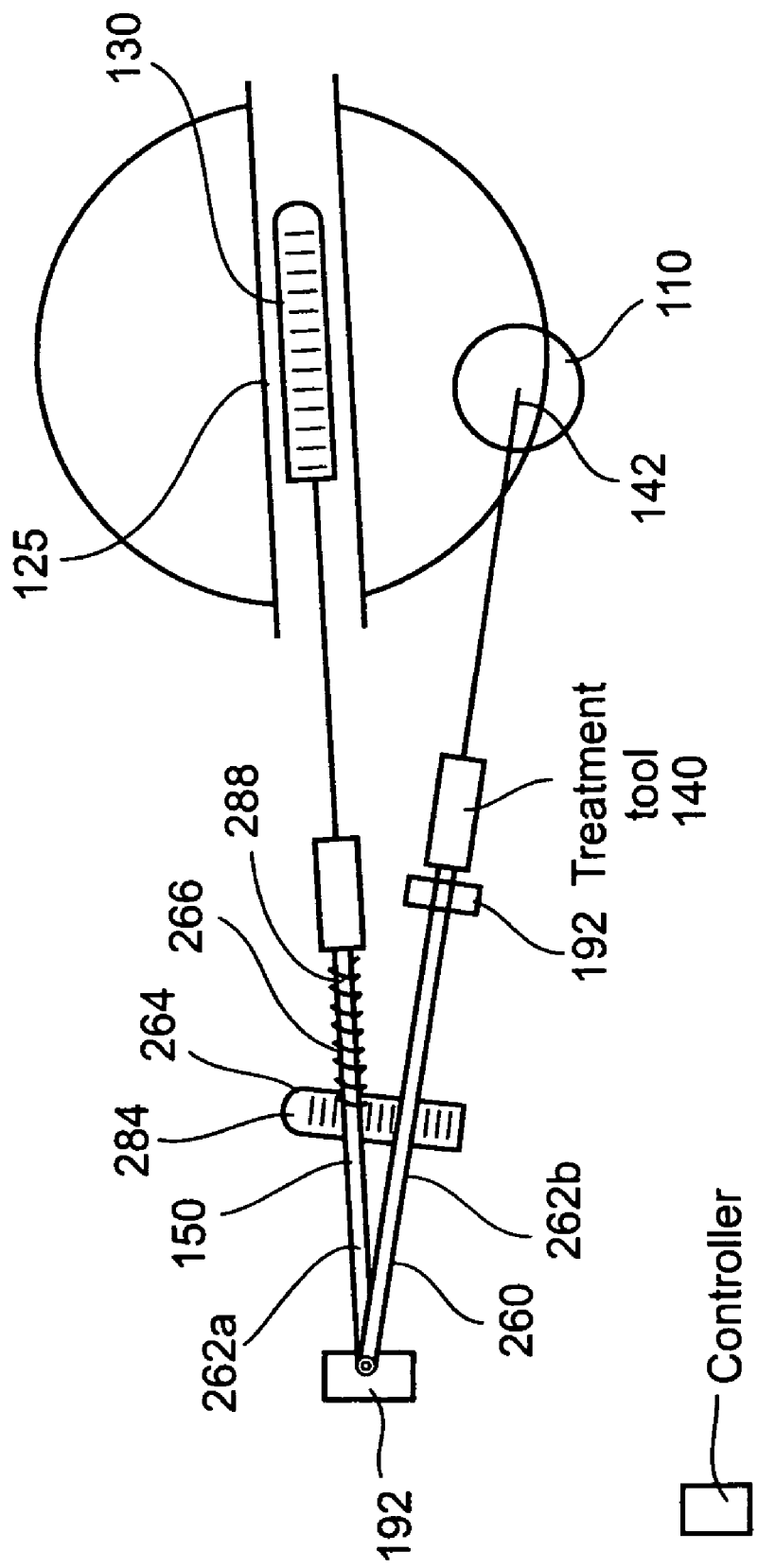

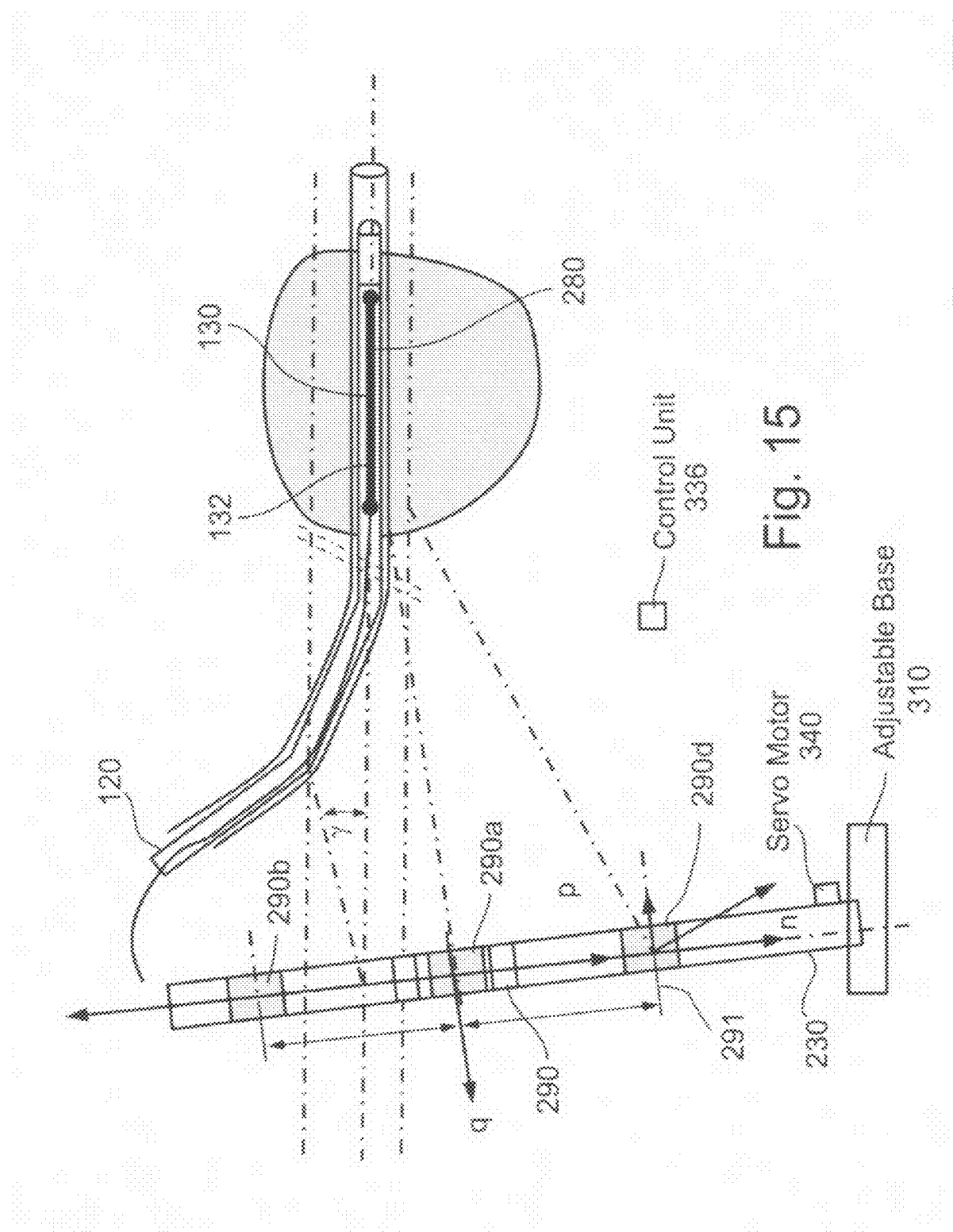

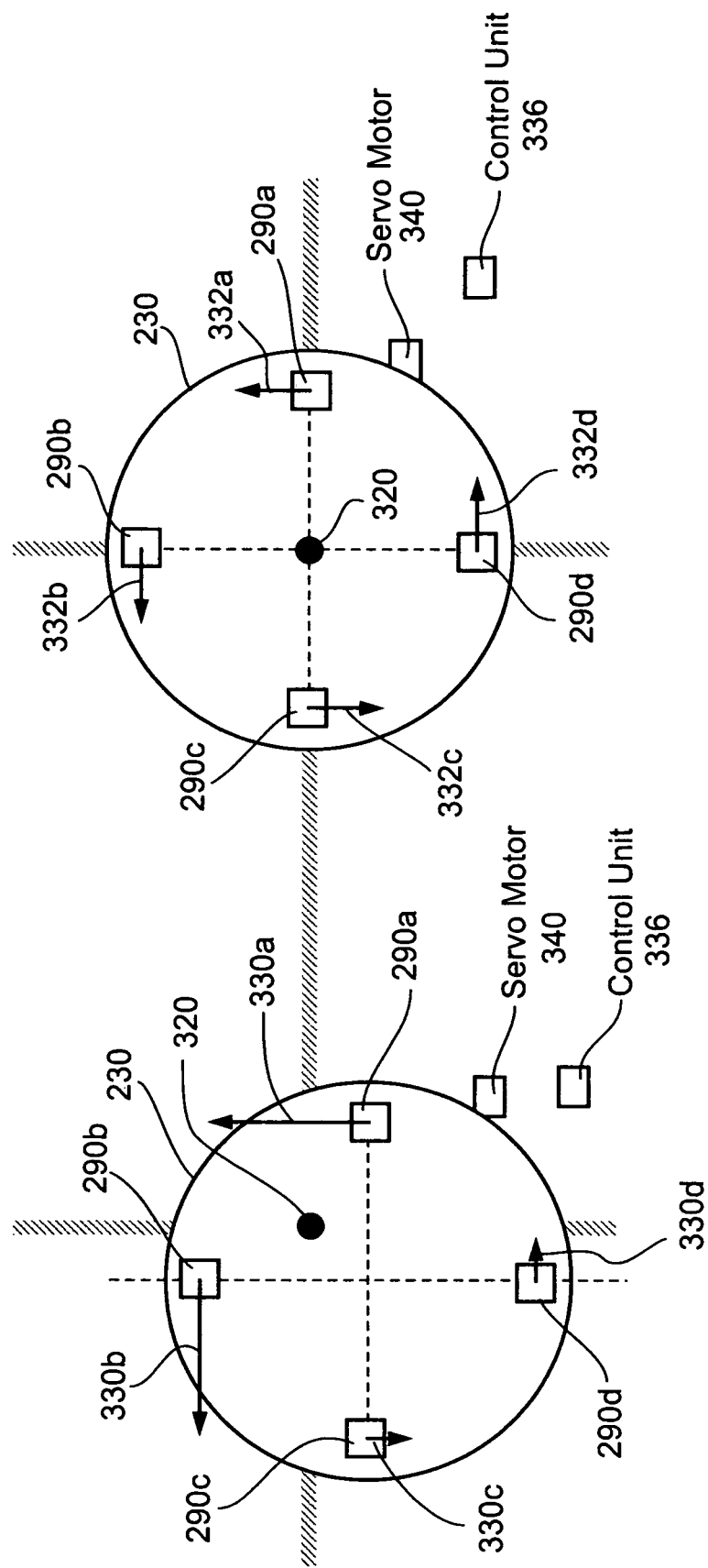

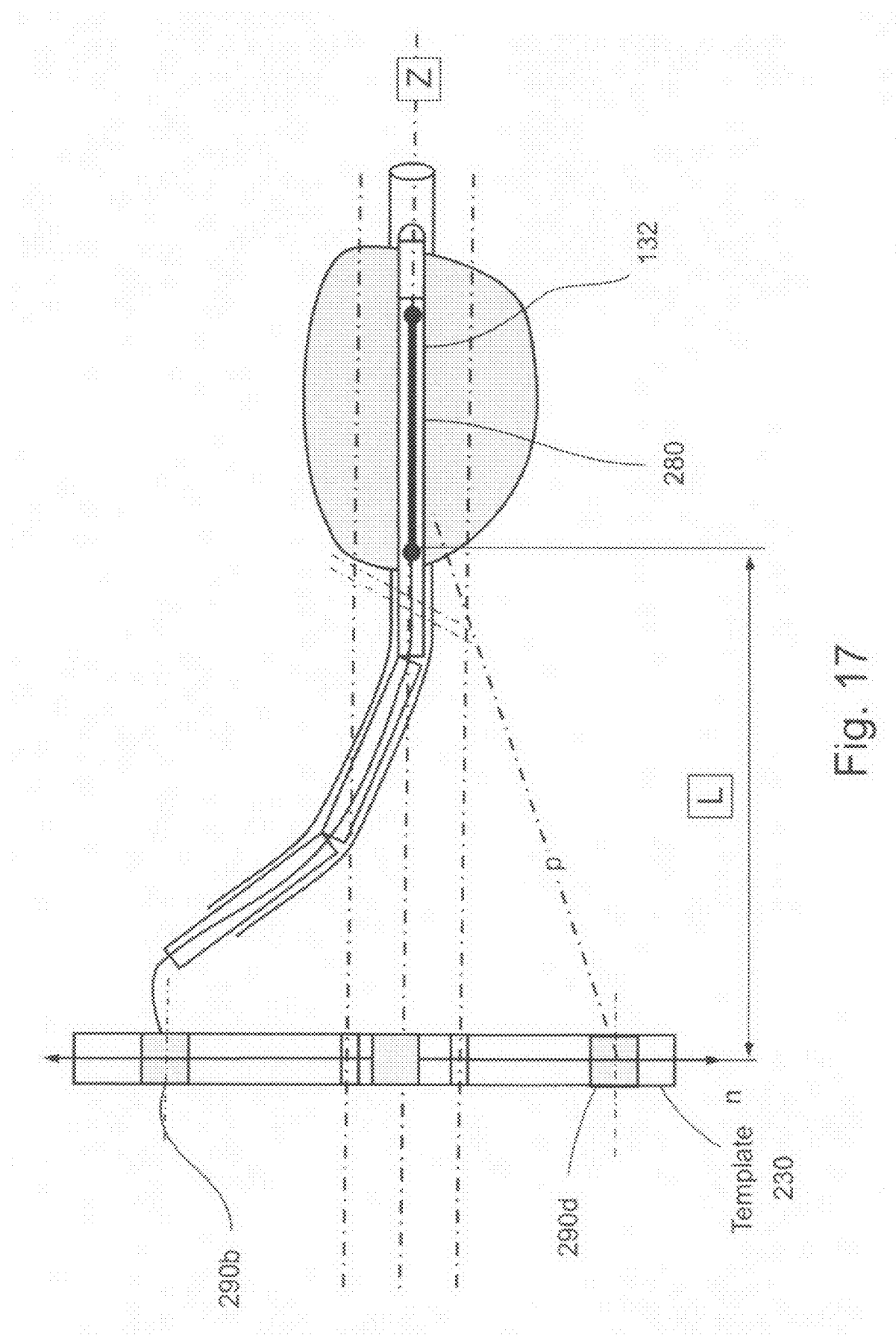

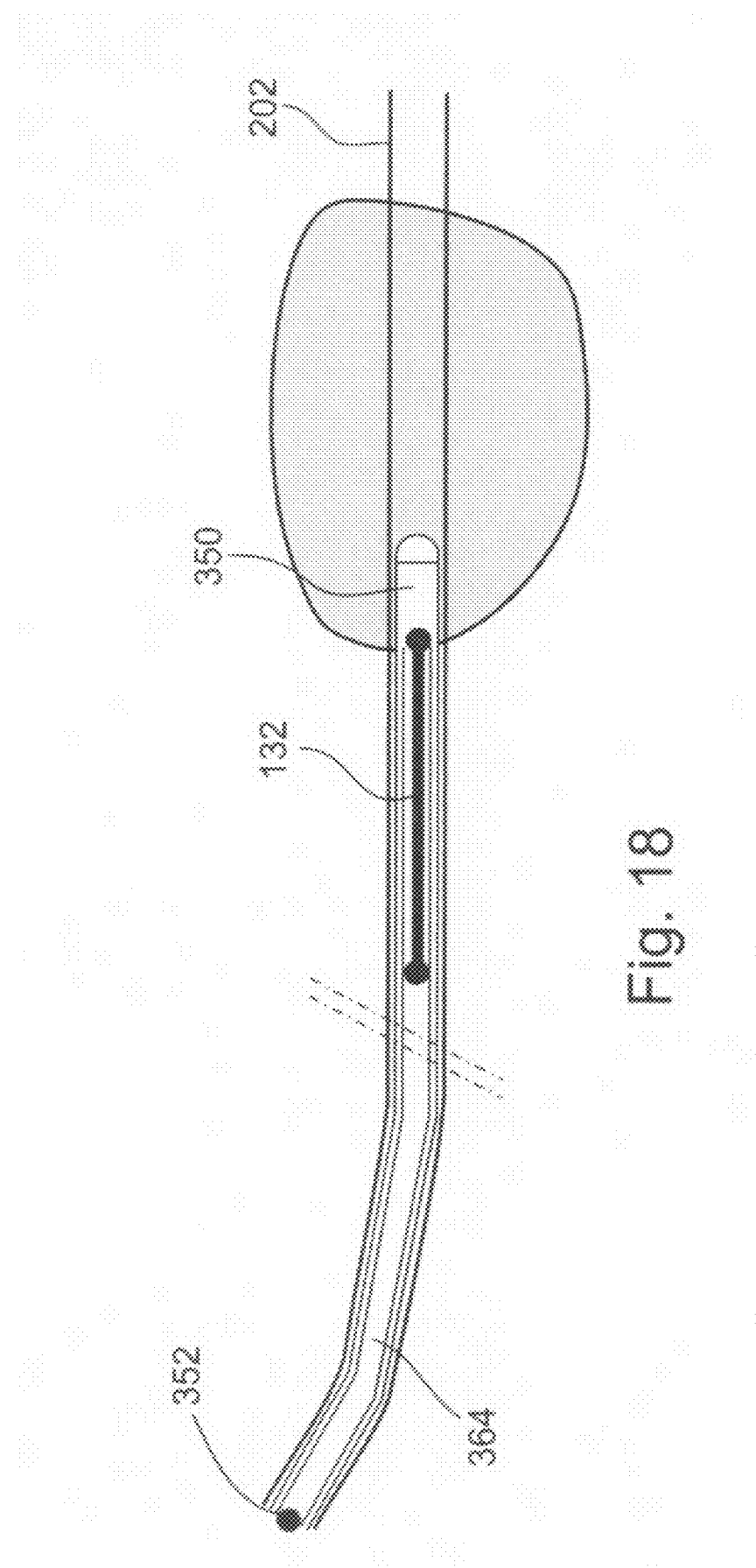

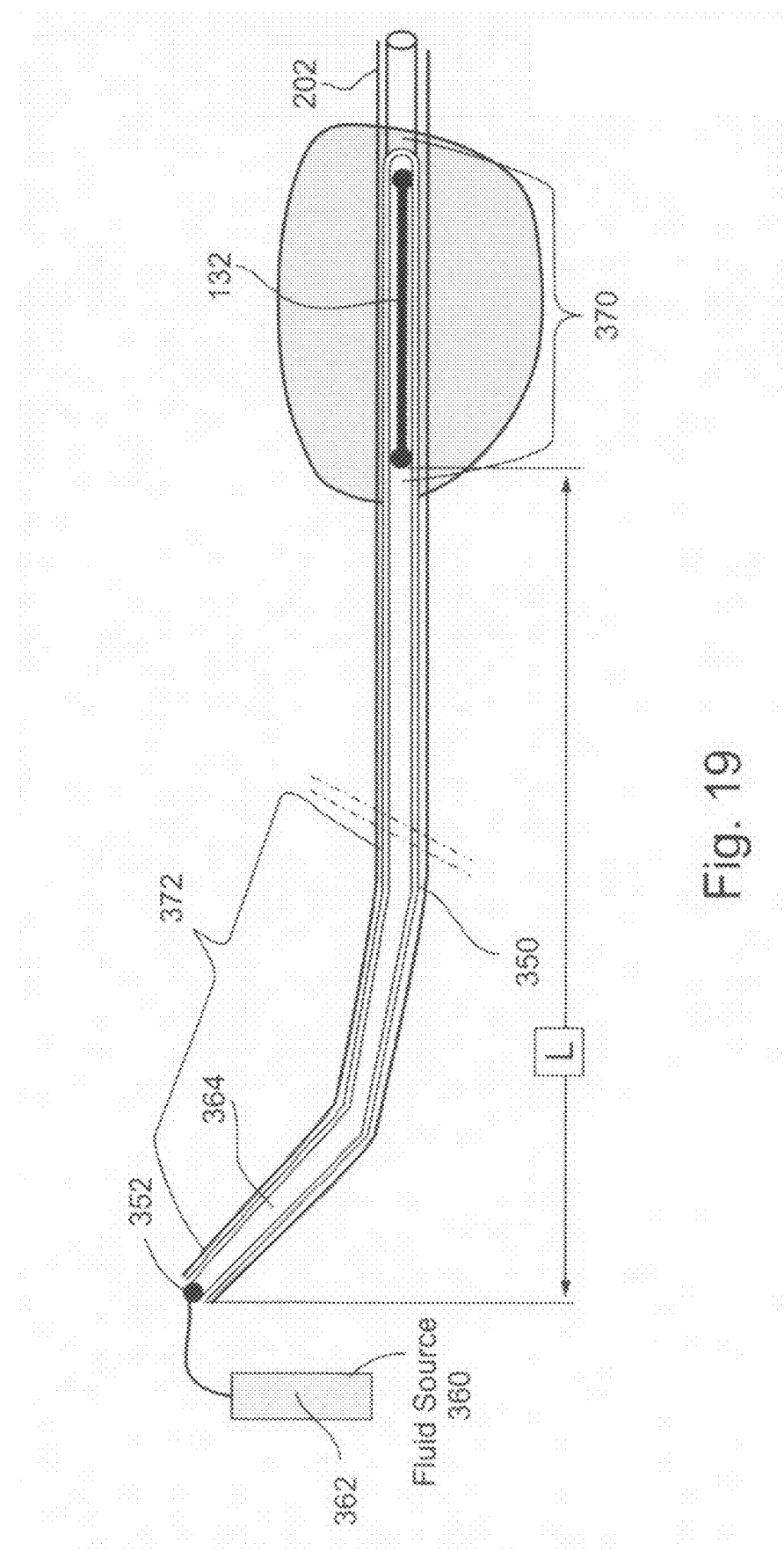

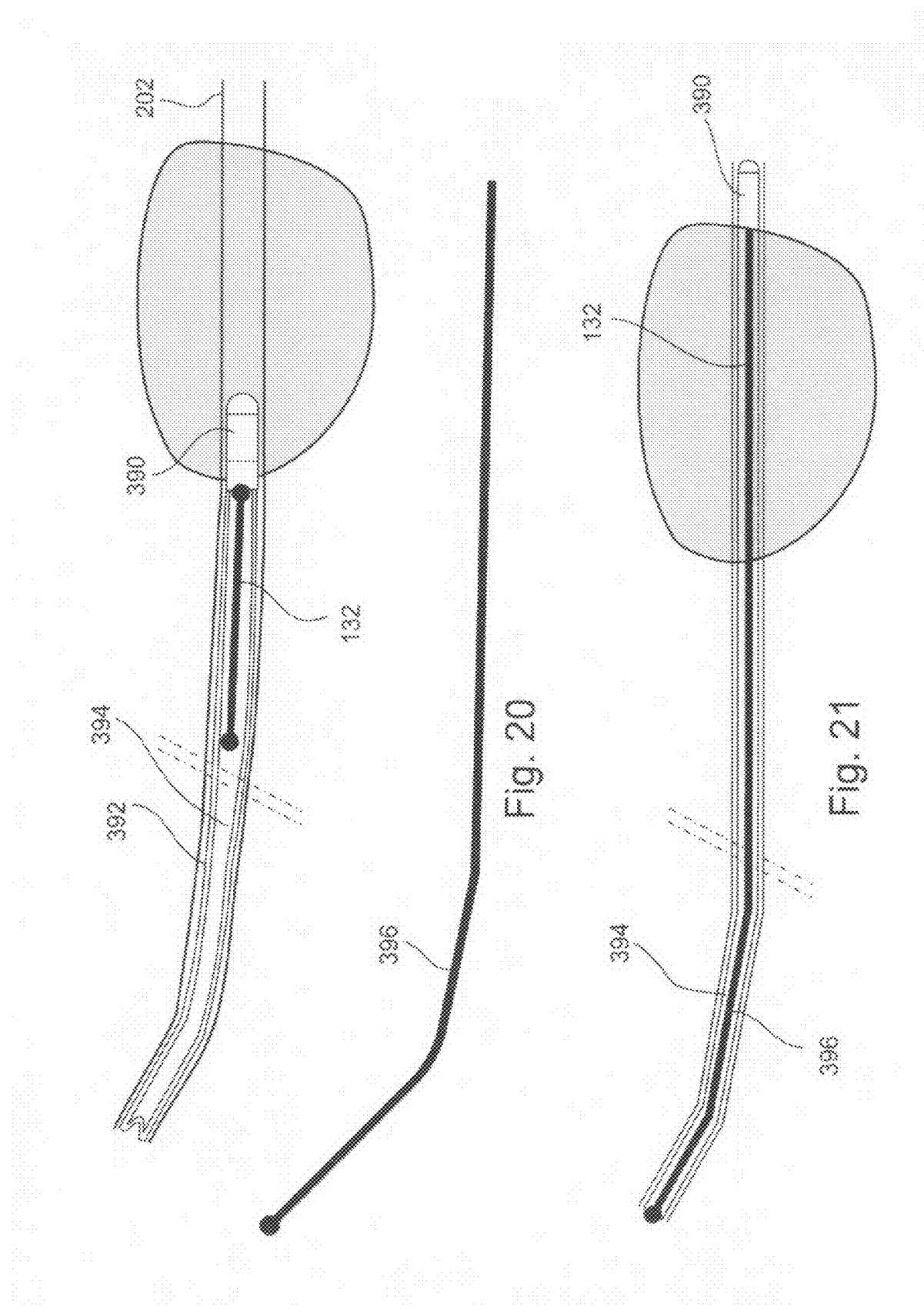

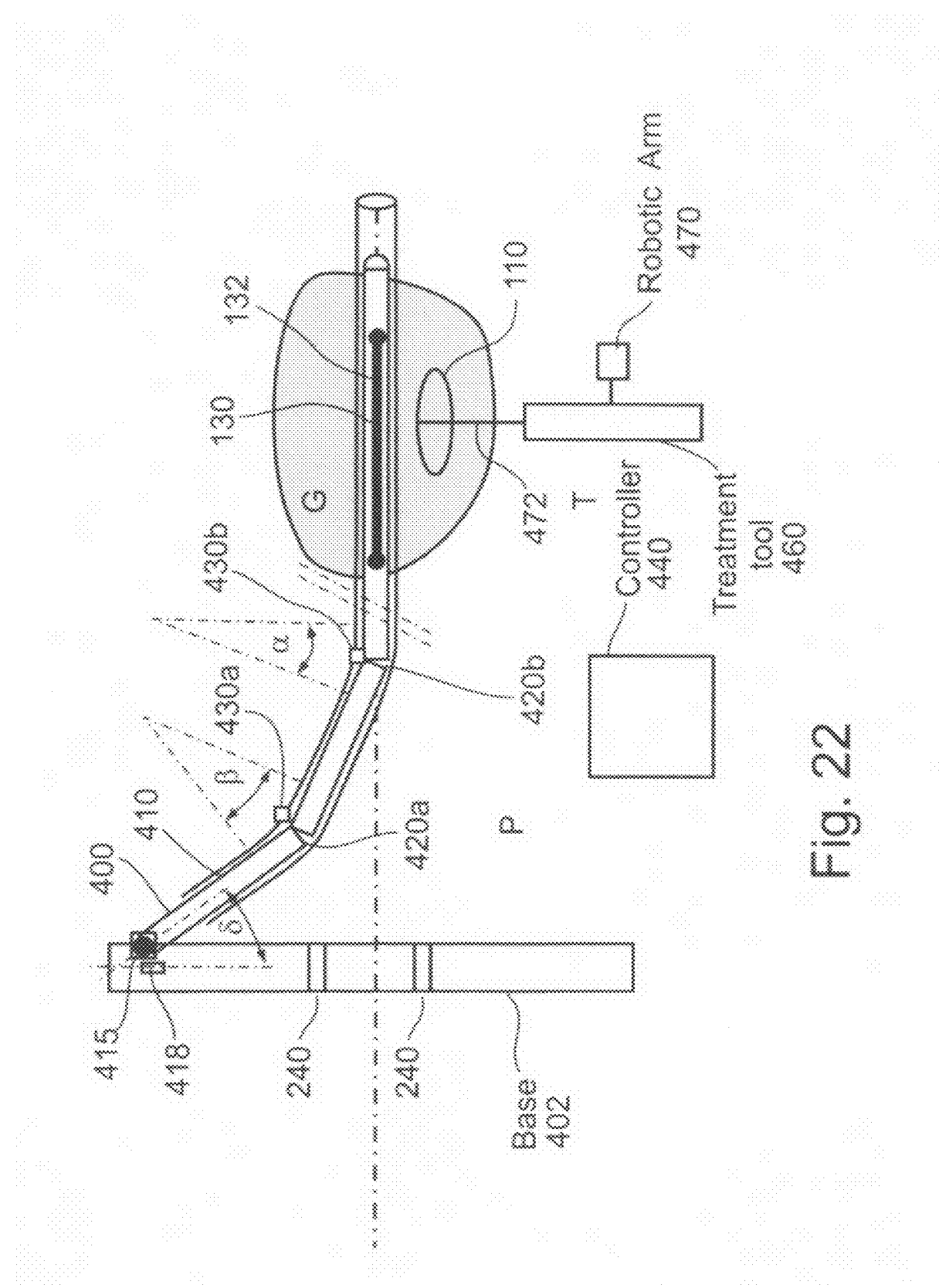

METHOD AND APPARATUS FOR POSITIONING A SURGICAL INSTRUMENT

This application is a National Phase Application of PCT/IL03/00540 having International Filing Date of 26 Jun. 2003, which claims priority from U.S. Provisional Patent Application No. 60/391,599 filed 27 Jun. 2002.

FIELD AND BACKGROUND OF THE INVENTION

The present invention relates to methods and apparatus for delivering a surgical instrument to a treatment site within the body of a patient. More particularly, the present invention serves to simplify surgical procedures for treating a variety of ailments, by enabling accurate placement of surgical tools in areas not directly visible to a surgeon during a surgical procedure, while reducing or eliminating need for real-time imaging modalities to guide placement of those surgical tools. Hence, the present invention finds uses in, for example, interventional cardiology, interventional gastrology, interventional urology, interventional gynecology, endoscopy and laparoscopy, as well as other medical disciplines.

Minimally-invasive surgery has become increasingly important in recent years. Surgical treatments which once required major surgical opening of body cavities, merely to provide a surgeon with access to a desired treatment site, are now increasingly operable utilizing what is known in the art as "minimally-invasive" surgical procedures, wherein surgical tools are introduced into the body through small openings or through naturally occurring body conduits, and thence are navigated to a treatment site where they are used to perform a therapeutic act. Minimally-invasive procedures minimize trauma to the body resulting from the process of delivering surgical tools to a desired intervention site, and avoid much of the damage, at loci distant from the desired treatment site, which once accompanied most surgical procedures. Damage which once endangered patients, engendered complications, increased mortality, caused discomfort and suffering, caused extended hospitalization, and led to long and complex periods of recuperation, can now largely be avoided in many cases.

Minimally-invasive procedures are, however, by their nature, procedures wherein the surgeon has limited ability to directly observe what he is doing. Surgical tools are manipulated from outside the body, yet perform their work inside the body. Tools designed to navigate the length of body conduits, endoscopes for example, are typically provided with electronic cameras to enable the surgeon to observe the treatment site from within the body conduit.

Delivering a surgical tool to a treatment site not located within a body conduit, however, is more complex. Typically, external imaging modalities such as CT, Ultrasound, Fluoroscope, static x-rays, or MRI must be used to steer the surgical tool to its treatment site. Yet, use of such imaging modalities during a surgical procedure is often complex and in some cases quite difficult. Each known imaging modality presents certain disadvantages: extended periods of fluoroscopy, for example, require extended exposure to pathogenic x-rays. Use of MRI in the operating room, for another example, comports restrictions on the types of surgical equipment that can be utilized during MRI operation.

There is thus a widely recognized need for, and it would be highly advantageous to have, a device and method for delivering a surgical tool to a treatment site, or for confirming the position a surgical tool at a treatment site, which method and device obviate the need for, or reduce dependence on, use of imaging modalities during treatment.

Benign Prostate Hyperplasia, or "BPH", which affects a large number of adult men, is a non-cancerous enlargement of the prostate. BPH frequently results in a gradual squeezing of the portion of the urethra that traverses the prostate, also known as the prostatic urethra. Squeezing of the prostatic urethra causes patients to experience a frequent urge to urinate because of incomplete emptying of the bladder, and a burning sensation or similar discomfort during urination. The obstruction of urinary flow can also lead to a general lack of control over urination, including difficulty initiating urination when desired, as well as difficulty in preventing urinary flow because of the residual volume of urine in the bladder, a condition known as urinary incontinence. Left untreated, the obstruction caused by BPH can lead to acute urinary retention (complete inability to urinate), serious urinary tract infections and permanent bladder and kidney damage.

Most males will eventually suffer from BPH. The incidence of BPH for men in their fifties is approximately 50% and rises to approximately 80% by the age of 80. The general aging of the United States population, as well as increasing life expectancies, is anticipated to contribute to the continued growth in the number of BPH sufferers.

Patients diagnosed with BPH generally have several options for treatment: watchful waiting, drug therapy, surgical intervention, including transurethral resection of the prostate (TURP), laser assisted prostatectomy and new less invasive thermal therapies.

Currently, of the patients suffering from BPH, the number of patients who are actually treated by surgical approaches is approximately 2% to 3%. Treatment is generally reserved for patients with intolerable symptoms or those with significant potential symptoms if treatment is withheld. A large number of the BPH patients delay discussing their symptoms or elect "watchful waiting" to see if the condition remains tolerable.

Thus, there is thus a widely recognized need for, and it would be highly advantageous to have, a device and method simplifying therapeutic intervention for relief of BPH, thereby making the procedure more attractive to potential patients and less complex and expensive for health providers, potentially resulting in a substantial increase in the number of BPH suffers who elect to receive interventional therapy.

SUMMARY OF THE INVENTION

According to one aspect of the present invention there is provided a method for delivering a treatment tool to a treatment site within the body of a subject in need thereof, the method comprising placing a guiding element at a reference site being at a first distance from the treatment site, the treatment site being in a first direction from the reference site; and utilizing a positioning tool to guide a treatment tool to a locus so positioned that a second distance, from the guiding element to the locus, is substantially similar to the first distance, and a second direction, from the guiding element to the locus, is substantially similar to the first direction from the reference site to the treatment site, thereby positioning the treatment tool substantially at the treatment site.

According to further features in preferred embodiments of the invention described below, the positioning tool is a mechanical device operable to position the treatment tool at the second distance from the guiding element and in the second direction from the guiding element, or an electromechanical device operable to position the treatment tool at the second distance from the guiding element and in the second direction from the guiding element, or a position-reporting device operable to report distance and direction from the guiding element to the treatment tool, thereby providing information enabling a surgeon to position the treatment tool at a the second distance from the guiding element and in the direction from the guiding element.

According to further features in preferred embodiments of the invention described below, the method further comprises using a catheter to place the guiding element at the reference site. Preferably the guiding element is integrated with the catheter. Preferably the reference site is a selected portion of a natural body conduit such as a urethra, a blood vessel, a bronchial tube, an intestine, or a colon.

Preferably 17 the positioning tool comprises a template having an aperture sized and shaped to permit passage of the treatment tool. The aperture may be sized and shaped to orient the treatment tool in a predetermined direction, which may be perpendicular to the template. Preferably the template comprises a plurality of apertures, each aperture sized and shaped to permit passage of a treatment tool.

Preferably the guiding element is a guiding segment which is substantially straight and has a length in excess of 1 cm.

Preferably, the method further comprises orienting the template to be perpendicular to a long axis of the guiding segment.

Preferably, the catheter comprises a plurality of joints lockable at fixed angles, or a plurality of variable joints joining rigid segments, each of the variable joints is operable to report an angle at which segments adjacent thereto are joined.

The method may further comprise orienting the template with respect to the guiding segment by attaching the template to the catheter at an angle calculated as a function of a sum of the reported angles of the plurality of variable joints.

The method may further comprise orienting the plane of the template by selecting a template position which minimizes a signal, received at a sensor mounted on the template, which signal originates at a signal transmitter proximate to the guiding segment.

The method may further comprise centering the template with respect to the guiding segment by selecting a template position which equalizes strengths of signals received at a plurality of sensors monitored on the template, which signals originate at a signal transmitter proximate to the guiding segment.

According to another aspect of the present invention there is provided a method for treating tissue at a treatment site within the body of a subject, comprising delivering a treatment tool to a treatment site within the body of a subject, by placing a guiding element at a reference site at a first distance from the treatment site, the treatment site being in a first direction from the reference site; and utilizing a positioning tool to guide a treatment tool to a locus so positioned that a second distance, from the guiding element to the locus, is substantially similar to the first distance, and a second direction, from the guiding element to the locus, is substantially similar to the first direction, thereby positioning the treatment tool substantially at the treatment site; and utilizing the treatment tool to treat the tissue at the treatment site.

According to further features in preferred embodiments of the invention described below, the method further comprises utilizing the treatment tool to ablating prostate tissue. The treatment site may be a volume of tissue situated less than a selected maximum distance from the guiding element and more than a selected minimum distance from the guiding element. The guiding element may be a guiding segment having a length in excess of 1 cm.

According to yet another aspect of the present invention there is provided a method for treating Benign Prostate Hyperplasia by ablating prostate tissue proximate to, but not contiguous to, a prostatic urethra, comprising:

a) utilizing a catheter to introduce into a prostatic urethra a substantially straight guiding segment oriented in a first orientation;

b) orienting a template having a plurality of apertures spaced around a central point, so that the template is perpendicular to the first orientation;

c) centering the template with respect to the guiding segment in such a way that a line, in the first orientation, extending from the guiding segment to the template, would intersect the template at the central point;

d) deploying a plurality of treatment tools through the plurality of apertures; and e) utilizing at least some of the treatment tools to ablate tissue of the prostate, thereby treating Benign Prostate Hyperplasia by ablating prostate tissue proximate to, but not contiguous to, a prostatic urethra.

According to still another aspect of the present invention there is provided an apparatus for delivering a treatment tool to a treatment site within the body of a subject, comprising:

a) a guiding element operable to be placed at a reference site at a first distance from the treatment site, the treatment site being in a first direction from the reference site; and b) a positioning tool operable to guide a treatment tool to a locus so positioned that a second distance, from the guiding element to the locus, is substantially similar to the first distance, and a second direction, from the guiding element to the locus, is substantially similar to the first direction from the reference site to the treatment site.

According to further features in preferred embodiments of the invention described below, the positioning tool is a mechanical device operable to position the treatment tool at the second distance from the guiding element and in the second direction from the guiding element, or an electromechanical device operable to position the treatment tool at the second distance from the guiding element and in the second direction from the guiding element, or a position-reporting device operable to report distance and direction from the guiding element to the treatment tool, thereby providing information enabling a surgeon to position the treatment tool at a the second distance from the guiding element and in the direction from the guiding element.

According to further features in preferred embodiments of the invention described below, the apparatus comprises a catheter operable to place the guiding element at the reference site. Preferably the guiding element is integrated with the catheter. Preferably the apparatus further comprises a treatment tool operable to ablate tissue. Preferably the guiding element is a guiding segment having a length in excess of 1 cm. Preferably the positioning tool comprises a template having an aperture sized and shaped to permit passage of the treatment tool. The aperture may be sized and shaped to orient the treatment tool in a predetermined direction, preferably perpendicular to the template.

Preferably, the template comprises a plurality of apertures, each aperture sized and shaped to permit passage of a treatment tool.

Preferably, the guiding element is a guiding segment which is substantially straight and has a length in excess of 1 cm.

Preferably the apparatus further comprises orienting means for orienting the template in an orientation perpendicular to a long axis of the guiding segment.

According to further features in preferred embodiments of the invention described below, the catheter comprises a plurality of joints lockable at fixed angles, or a plurality of variable joints joining rigid segments, each of the variable joints is operable to report an angle at which segments adjacent thereto are joined.

The apparatus may further comprise a servomotor operable to orient the template perpendicularly to the guiding segment. The servomotor may be operable to orient the template with respect to the catheter at an angle calculated as a function of a sum of the reported angles of the plurality of variable joints.

Preferably, the guiding element comprises a signal transmitter and the template comprises a signal sensor. The signal sensor may be operable to report a signal whose strength is a function of an angle of orientation of the template with respect to the guiding segment. The signal sensor may be operable to report a signal whose strength is at a minimum when the template is perpendicular to the guiding segment.

The apparatus may further comprise a plurality of sensors operable to receive a signal generated by the signal transmitter. Preferably, the plurality of sensors is operable to report substantially equal signal strengths when the template is both perpendicular to, and centered with respect to, the guiding element.

According to further features in preferred embodiments of the invention described below, the catheter is operable to be flexible, and also operable to be stiff.

According to further features in preferred embodiments of the invention described below, the catheter comprises an inflation lumen, and the catheter is operable to be rendered stiff by introduction of pressurized fluid into the inflation lumen. The catheter may be operable to be stiffened by insertion of an insertable stiffening element.

According to further features in preferred embodiments of the invention described below, the guiding element comprises a transmitter. Preferably, the guiding element comprises a sensor operable to detect a signal transmitted by the signal transmitter and reflected from a treatment tool. Alternatively, a treatment tool comprises a sensor operable to detect a signal transmitted by the transmitter.

According to further features in preferred embodiments of the invention described below, the guiding element comprises a sensor, and a treatment tool comprising a transmitter, the sensor is operable to detect a signal transmitted by the transmitter.

According to further features in preferred embodiments of the invention described below, the apparatus further comprises a display system operable to receive information from said sensor, and a controller operable to calculate movements required to deliver said treatment tool to said treatment site, based on information provided by said sensor.

According to an additional aspect of the present invention there is provided an apparatus for delivering a treatment tool to a treatment site in the body of a subject, comprising:

a) an imaging device;

b) a catheter which comprises a guiding element designed and constructed to be rendered visible by the imaging system, and to appear distinct from other objects imaged by the imaging system; and c) a treatment tool which comprises a distal portion designed and constructed to be rendered visible by the imaging system, and to appear distinct from other objects imaged by the imaging system.

The present invention successfully addresses the shortcomings of the presently known configurations by providing a method and apparatus for delivering a treatment tool to a treatment site within the body of a patient, without requiring use of imaging modalities during the surgical operation.

The present invention further successfully addresses the shortcomings of the presently known configurations by providing methods and apparatus for treating Benign Prostate Hyperplasia which are simpler and less costly to execute than are the methods of prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Figure, like numbers refer to like components.

In the drawings:

FIG. 1 is a simplified schematic of an apparatus for delivering a treatment tool to a treatment site, according to an embodiment of the present invention;

FIG. 2A is a simplified schematic of a prostate requiring treatment for BPH, showing an elongated guiding element, according to an embodiment of the present invention;

FIG. 2B is a simplified schematic of a prostate requiring treatment for BPH, showing an elongated guiding element and a positioning device, according to an embodiment of the present invention;

FIG. 3 is a simplified schematic of a positioning tool embodied as a template, according to an embodiment of the present invention;

Figure 4:
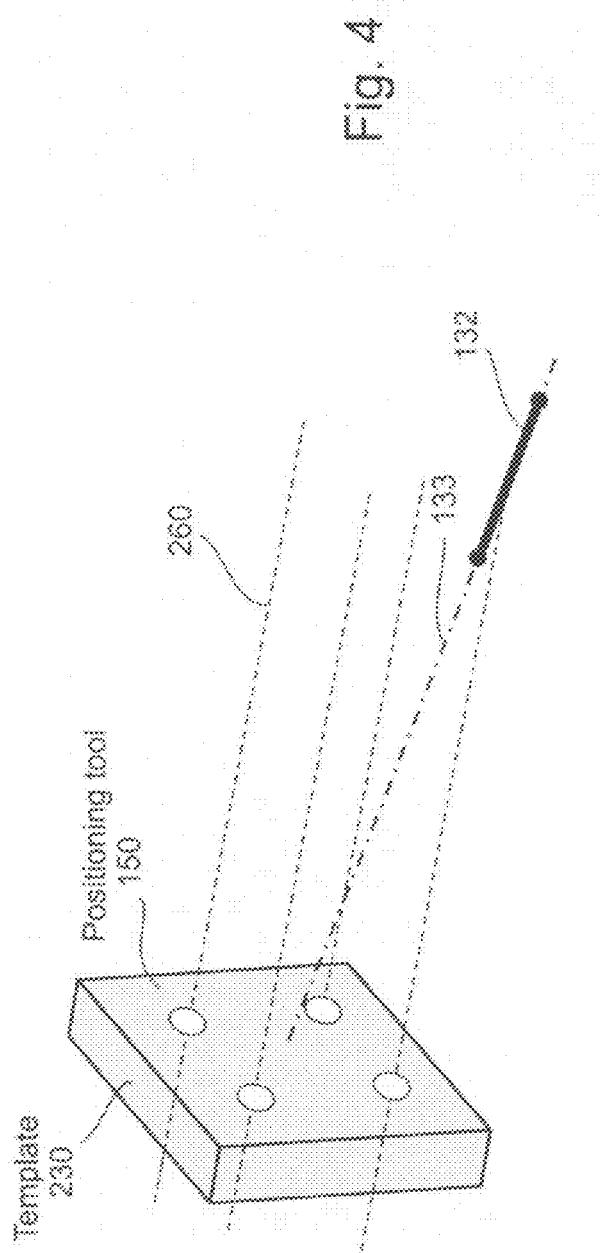
Figure 5:
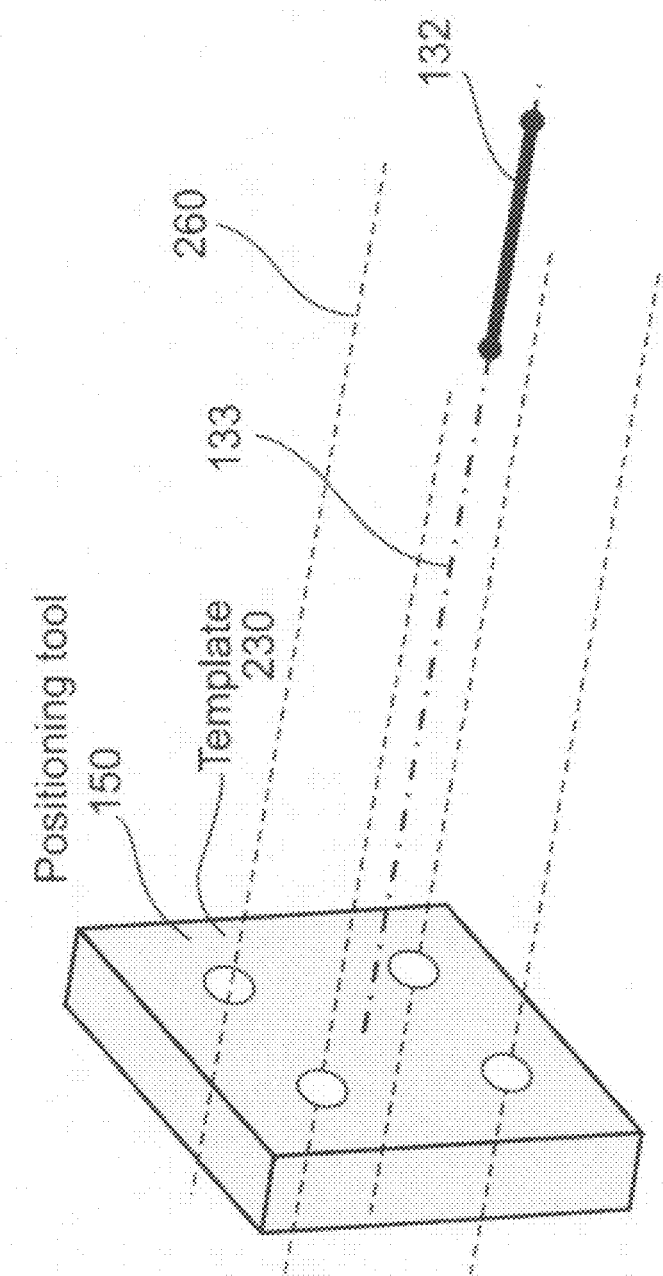
Figure 6:
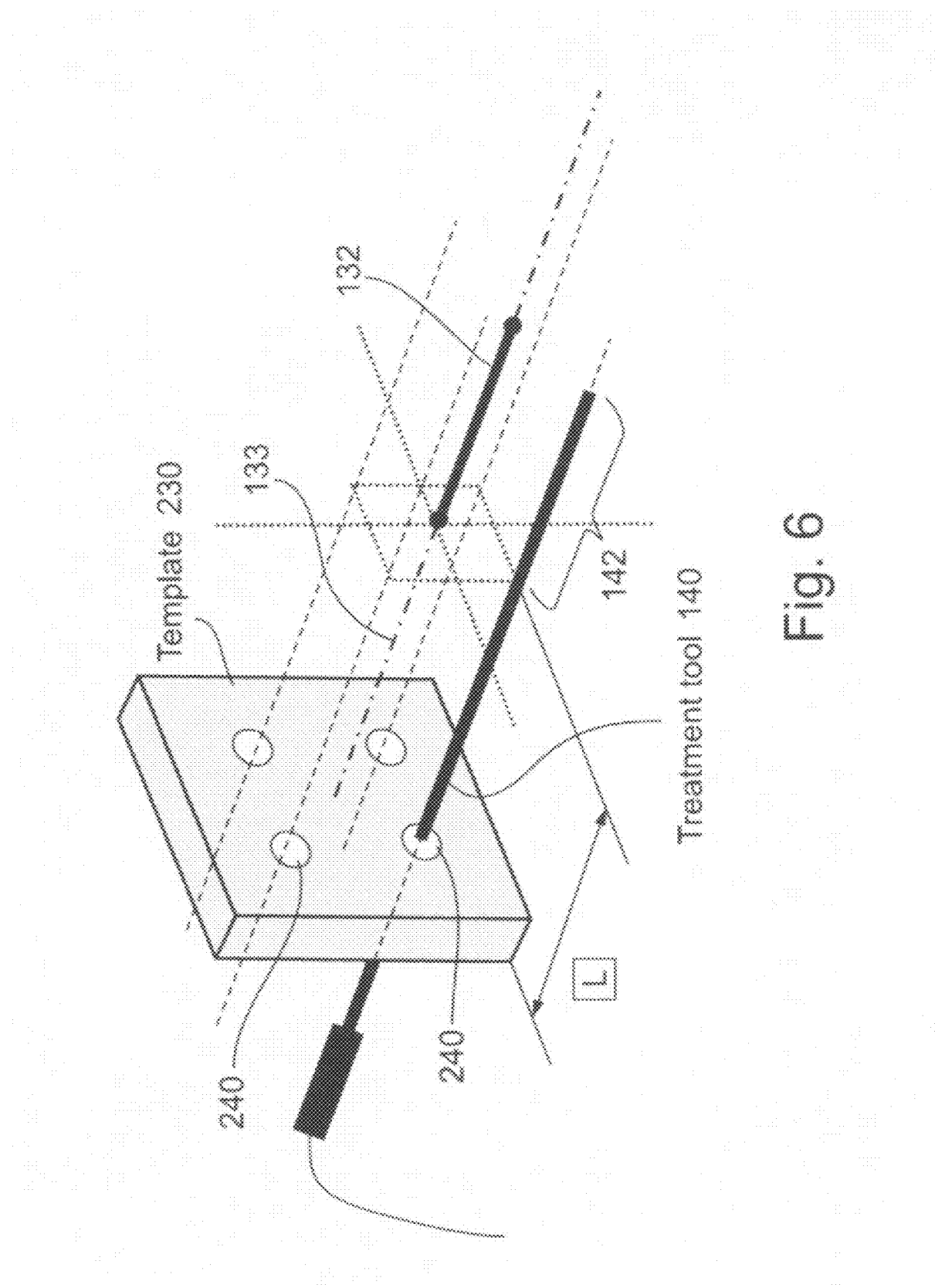
Figure 10:
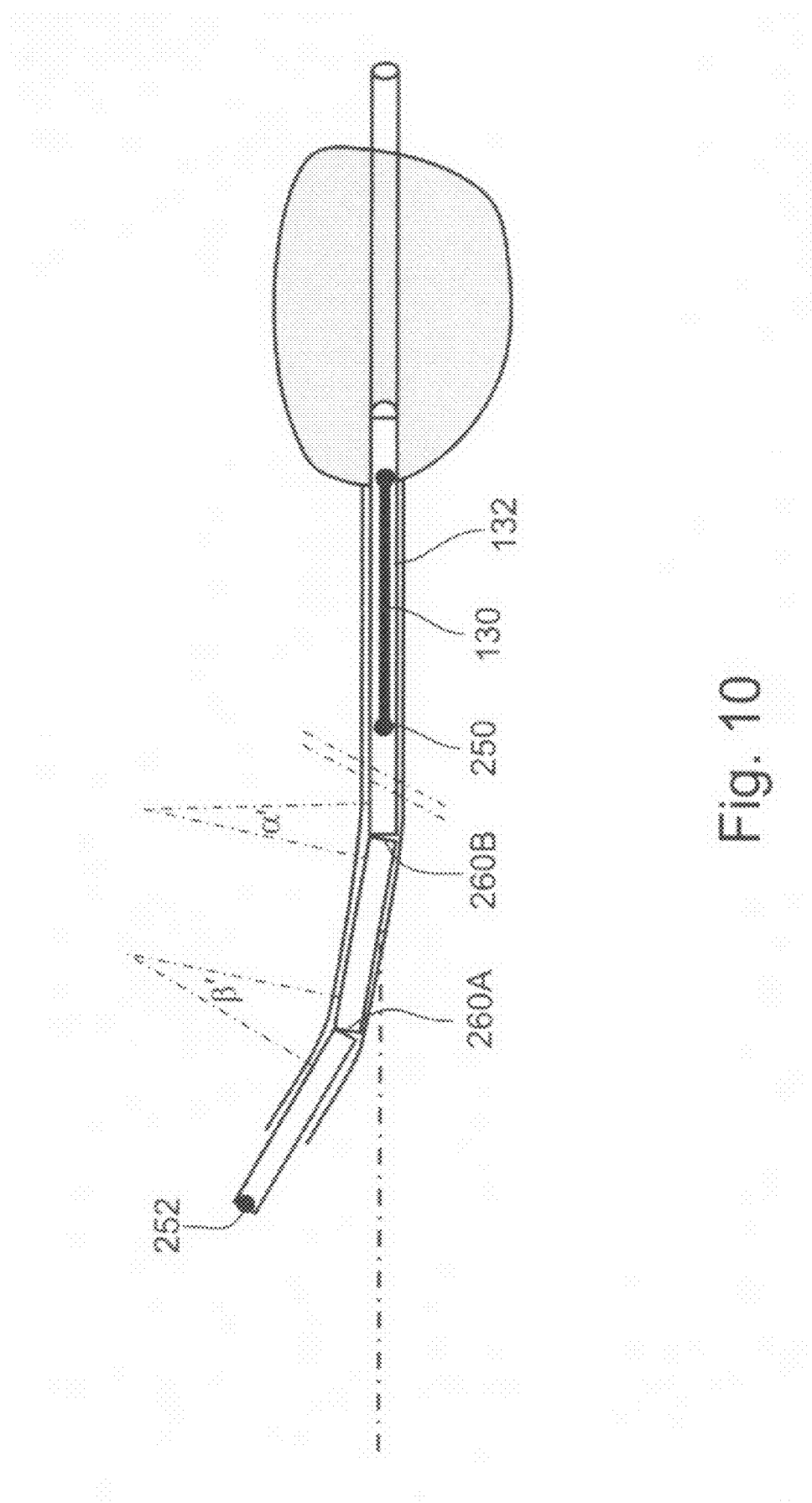
Figure 11:
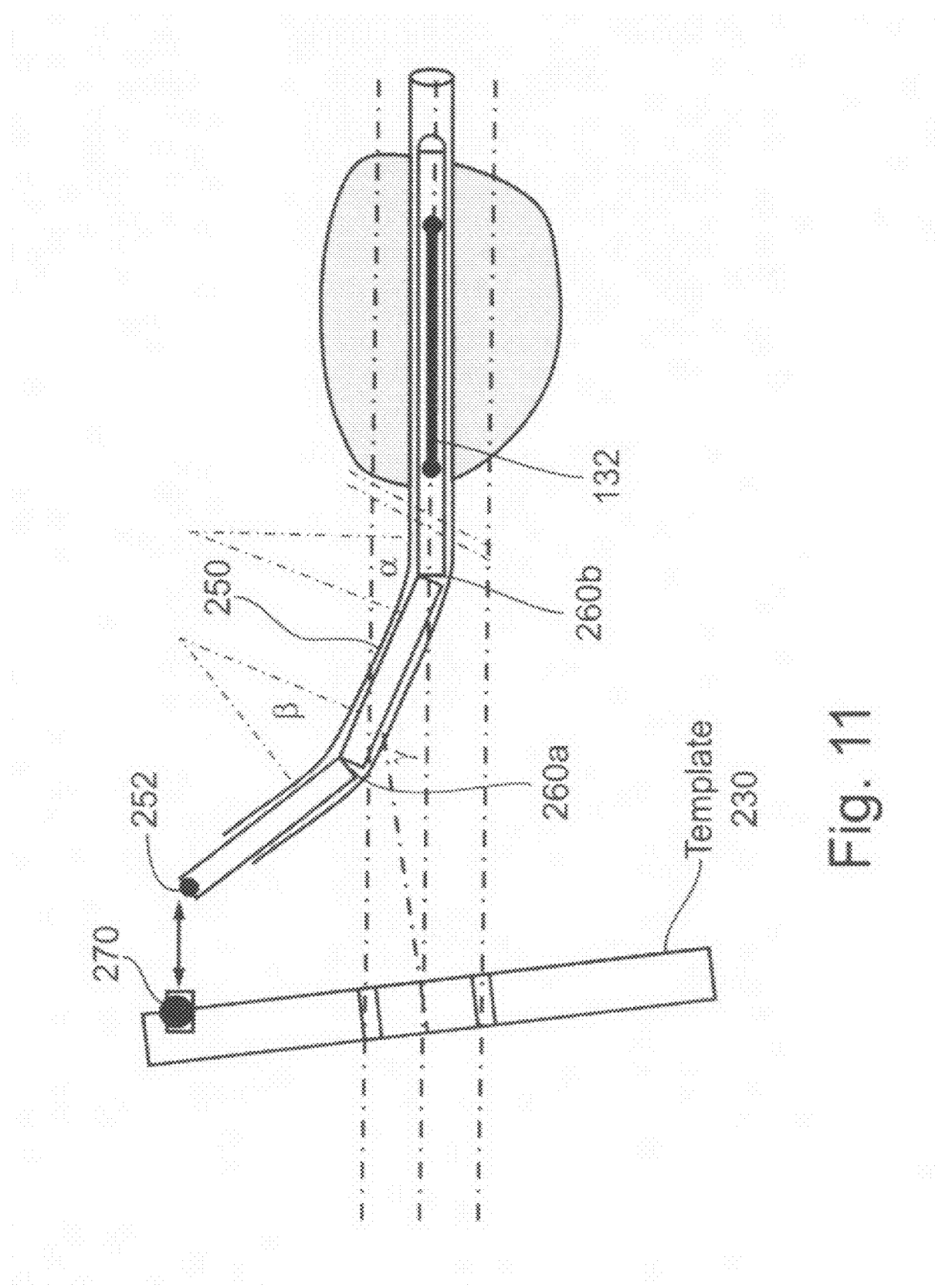
Figure 12:
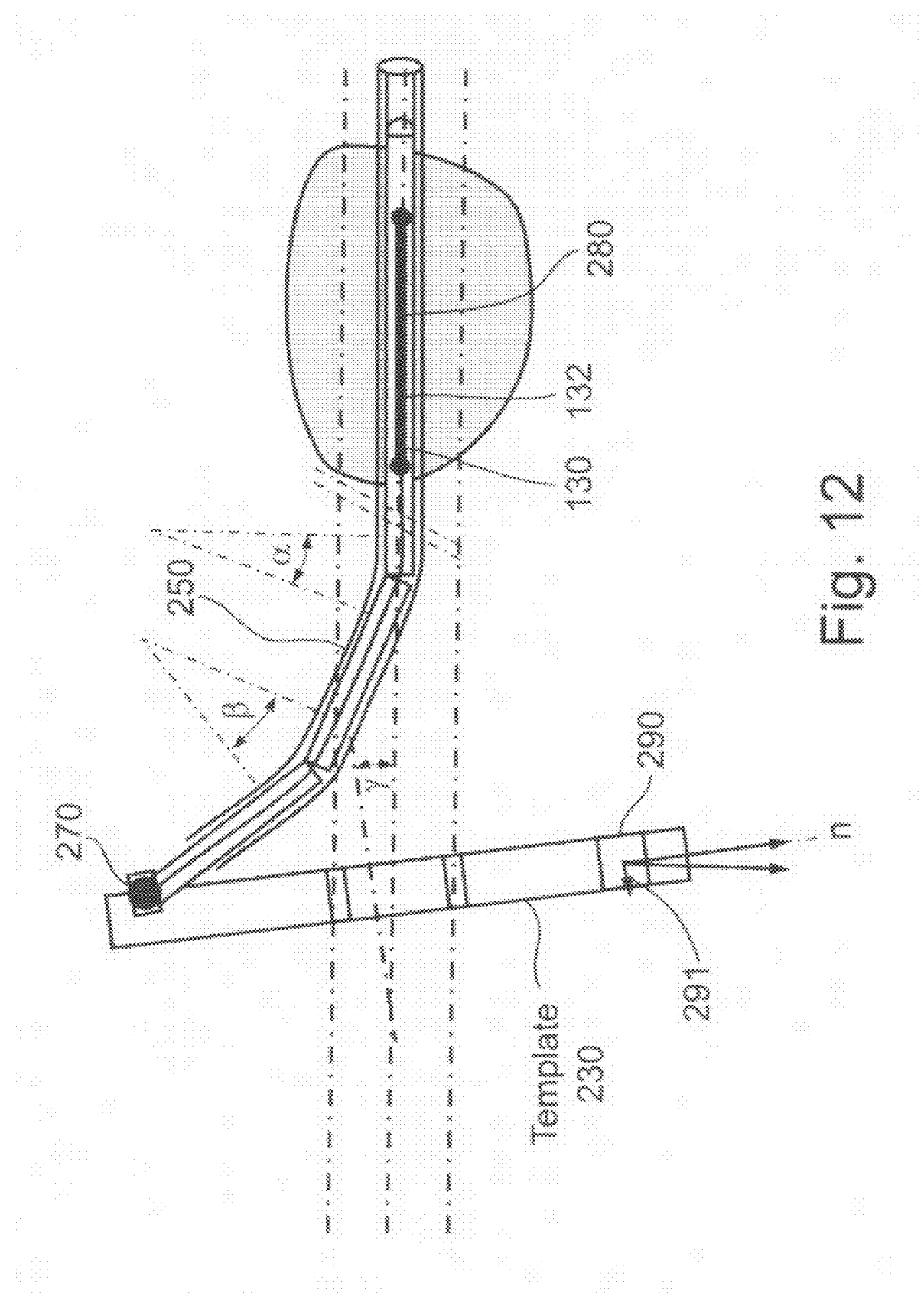
Figure 13:
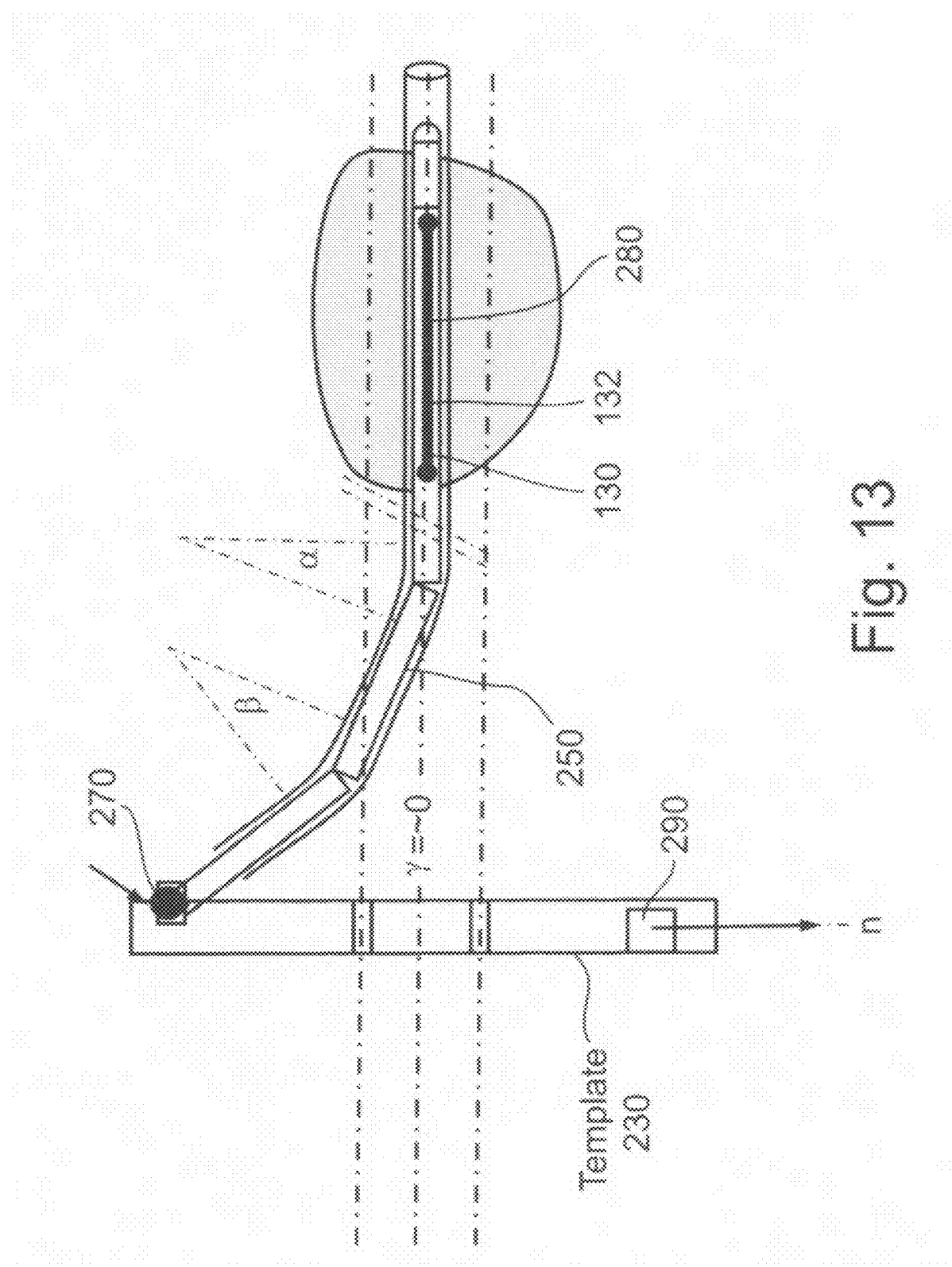
Figure 14:
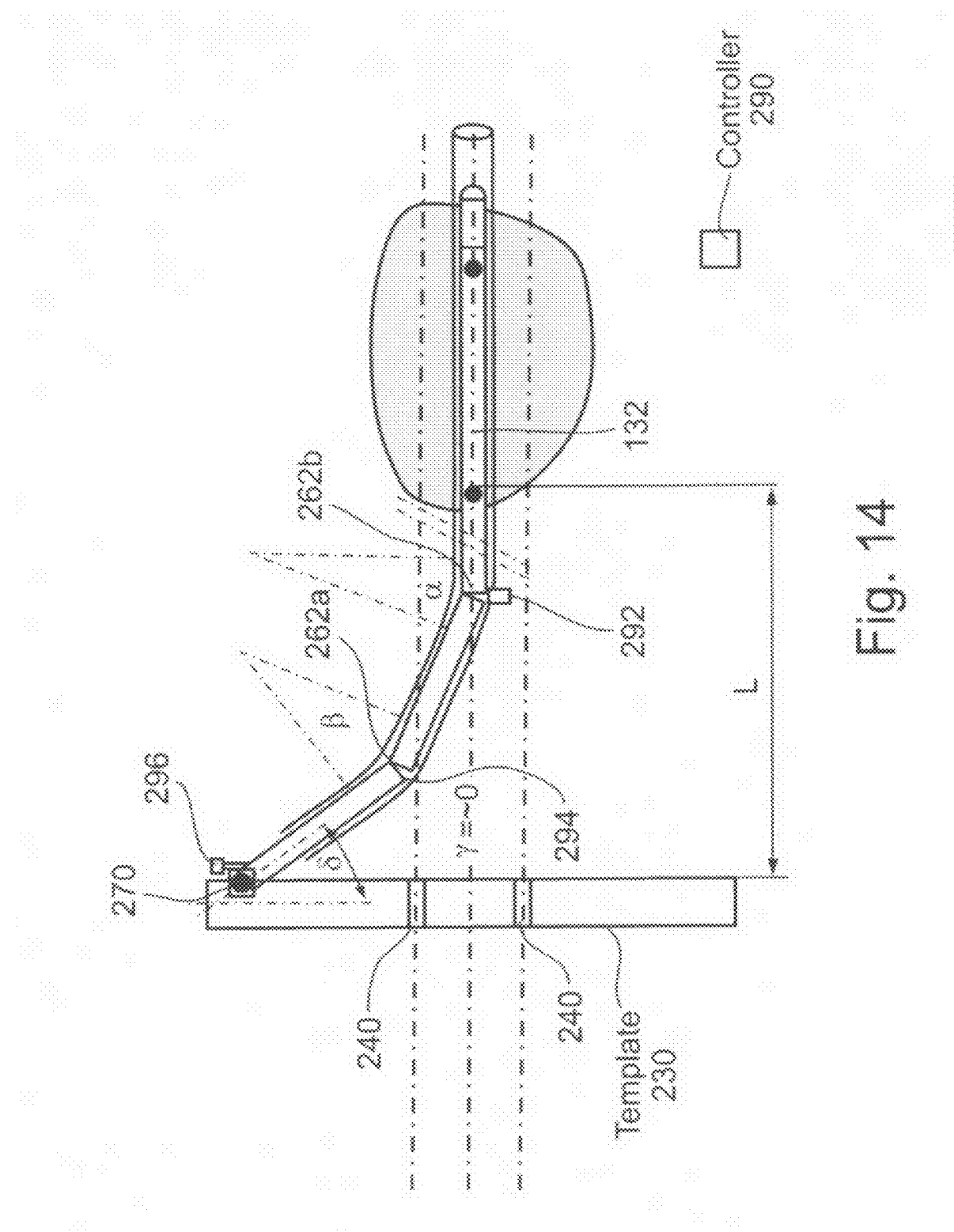
Figure 23:
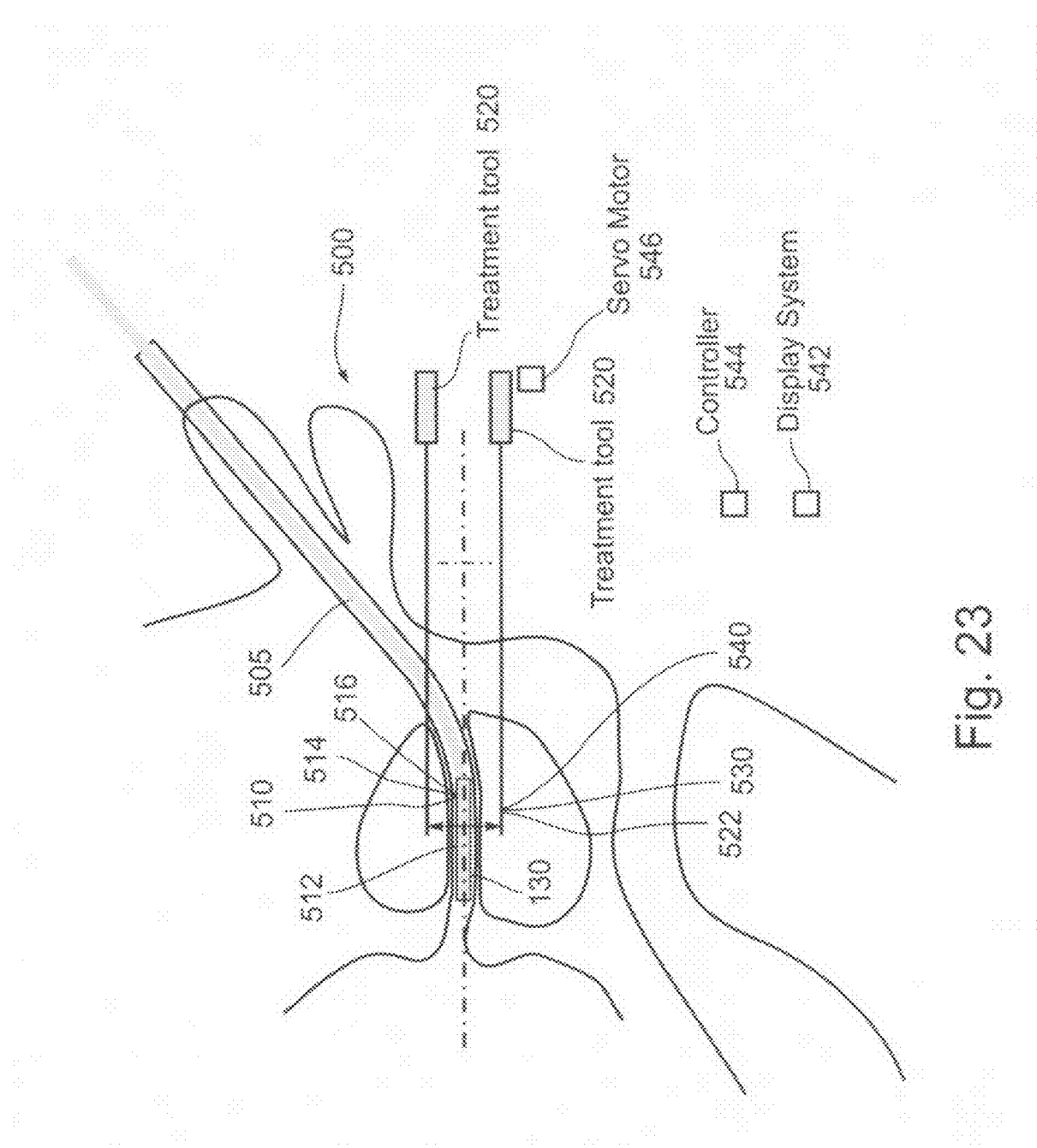
Figure 24:
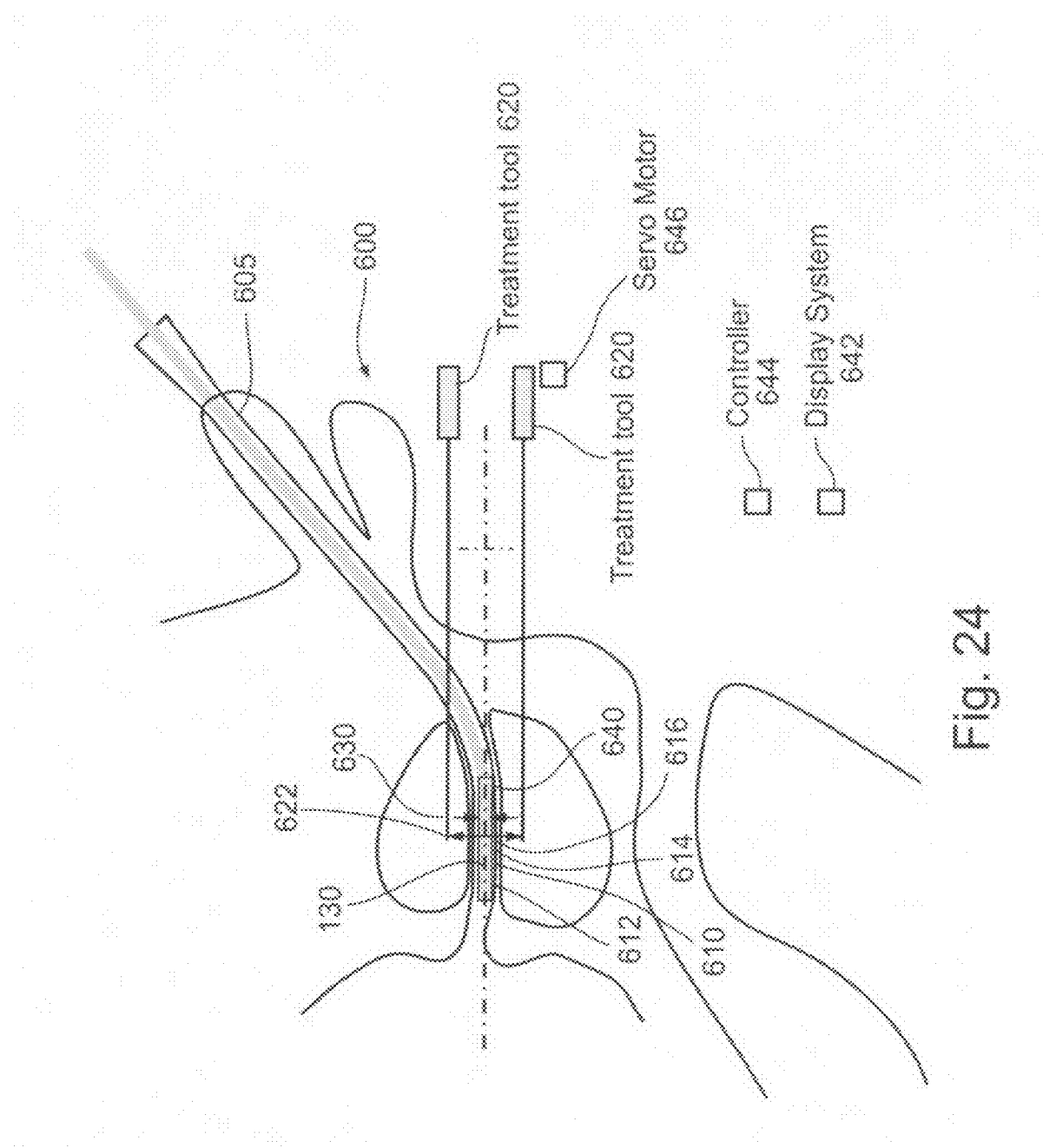
Figure 25:
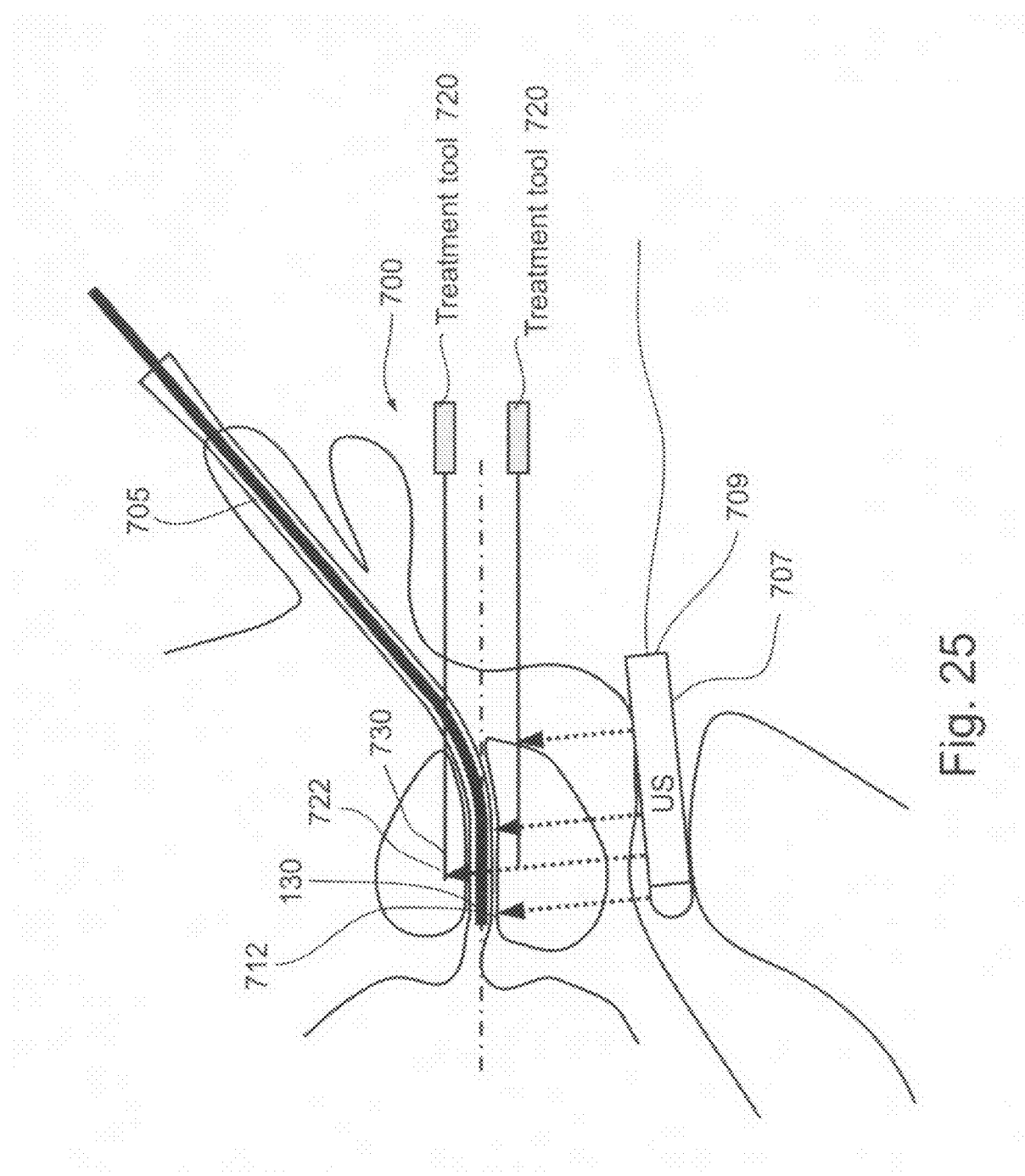

FIG. 4 presents a step in a process of aligning a guiding segment and a template with respect to each other, according to an embodiment of the present invention;

FIG. 5 presents an additional step in a process of aligning a guiding segment and a template with respect to each other, according to an embodiment of the present invention;

FIG. 6 presents a treatment tool passed through an aperture of a template oriented with respect to a guiding segment installed at a reference site, according to an embodiment of the present invention;

FIG. 7 presents a plurality of treatment tools held parallel to a guiding segment, according to an embodiment of the present invention;

FIG. 8 presents a plurality of treatment tools held parallel to a guiding segment, as seen from an "end-on" perspective, according to an embodiment of the present invention;

FIG. 9 presents a simplified schematic of an alternative construction of a positioning tool, according to an embodiment of the present invention;

FIG. 10 presents a simplified schematic of a multi-joint locking catheter, according to an embodiment of the present invention;

FIG. 11 presents a stage in use of a multi-joint locking catheter, according to an embodiment of the present invention;

FIG. 12 presents an additional stage in use of a multi-joint locking catheter, according to an embodiment of the present invention;

FIG. 13 presents an additional stage in use of a multi-joint locking catheter, according to an embodiment of the present invention;

FIG. 14 presents an alternative configuration for achieving perpendicular orientation of a template with respect to a guiding segment, according to an embodiment of the present invention;

FIG. 15 presents yet another configuration for orienting a template with respect to a guiding element, according to an additional embodiment of the present invention;

FIGS. 16A and 16B provide simplified additional views of a template, showing sensors mounted thereon, according to an embodiment of the present invention;

FIG. 17 presents a side view of a detached-template configuration of a positioning tool, according to an embodiment of the present invention;

FIG. 18 is a simplified schematic of a flexible self-stiffening catheter shown during insertion into a urethra of a prostate, according to a further embodiment of the present invention;

FIG. 19 is a simplified schematic of a catheter in a stiffened state, according to an embodiment of the present invention;

FIG. 20 is a simplified schematic of a flexible catheter having an insertable stiffening element, according to a further embodiment of the present invention;

FIG. 21 is an additional simplified schematic of a flexible catheter having an insertable stiffening element, according to a further embodiment of the present invention;

FIG. 22 is a simplified schematic of a treatment tool positioning apparatus, according to a further embodiment of the present invention;

FIG. 23 is a simplified schematic of a treatment tool positioning apparatus incorporating an energy transmitter and an energy detector, according to an embodiment of the present invention;

FIG. 24 is a simplified schematic of a treatment tool positioning apparatus incorporating an energy transmitter co-located with an energy sensor, according to an additional embodiment of the present invention; and FIG. 25 is a simplified schematic of a treatment tool positioning apparatus operable in conjunction with a conventional imaging device, according to an additional embodiment of the present invention.

DESCRIPTION OF THE PREFERRED EMBODIMENTS

The present invention is of a method and apparatus for positioning a surgical tool at a treatment site within the body of a patient. Specifically, the present invention can be used during a minimally-invasive surgical procedure to direct a surgical treatment tool to a desired treatment site, for diagnosis or for surgical treatment at that site, while reducing dependance on real-time use of imaging modalities during positioning of the tool.

The principles and operation of a surgical treatment tool placement system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The phrase "treatment site" is used herein to refer to a tissue, organ, or portion of an organ that a surgeon desires to treat during a surgical procedure. For example, in the case of a tumor that a surgeon desires to ablate, the tumor itself and possibly a portion of surrounding tissue, at the discretion of the surgeon, would be the "treatment site".

The phrases "surgical tool" and "treatment tool" are used herein to refer to any instrument or set of instruments used by a surgeon to diagnose or to treat tissues at the treatment site. Typically, a treatment tool is an instrument designed to transfer energy at the treatment site, such as a needle-shaped cryoprobe operable to cool tissues to cryoablation temperatures, or a probe capable of dispensing radio-frequency or microwave radiation, or a probe operable to ablate tissues through electrical heating or other forms of heating. Yet the phrase "treatment tool" is not limited to instruments for energy transfer. A diagnostic tool such as a short-distance imaging tool (e.g., local MRI) is a "treatment tool" as that phrase is used herein.

The phrase "reference site" is used herein to refer to a site within a patient's body, which site has a known spatial relationship to a treatment site within that body. Preferably, a reference site is also a site accessible to easy access from outside the body, through a body conduit for example. Thus, for example, the portion of a urethra passing through an enlarged prostate might be an appropriate reference site for an operation intended to reduce prostate volume, since that portion of the urethra has a fixed and known spatial relationship to the prostate through which it passes.

The phrase "guiding element" is used herein to refer to an object which, according to an embodiment of the present invention, is placed at (or within) a reference site, and which may be used, possibly in conjunction with additional tools, to guide a treatment tool to a treatment site, position a treatment tool at a treatment site, or verify the positioning of a treatment tool at a treatment site.

The phrase "target locus" is used herein to refer to a spatial locus, a volume defined by its spatial relationship to an installed guiding element, towards which a treatment tool is directed.

As used herein the terms "about" and "substantially similar" refer to ±10% preferably, ±5%, more preferably, ±2%, most preferably, ±0.1-1.0%.

An embodiment of the present invention involves guiding a treatment tool to a treatment site by a) placing a guiding element at a reference site within a body of a patient, the reference site having a known spatial relationship to the treatment site, and b) utilizing a positioning tool to guide a treatment tool to a locus so positioned with respect to that guiding element that the spatial relationship between that guiding element and that locus is substantially similar to the spatial relationship known to exist between the reference site and the treatment site, thereby positioning the treatment tool substantially at the treatment site.

Of course, in typical use, having guided a treatment tool to a treatment site, a surgeon will generally activate that treatment tool to produce a therapeutic effect, such as ablation of tissue, at that treatment site.

As described in the following, the positioning tool is preferably a mechanical, electro-mechanical, or electronic device for positioning the treatment device at a selected distance from the guiding device and in a selected direction from the guiding device. Alternatively, the positioning tool may be a mechanical, electromechanical or electronic device for reporting the position of a treatment tool with respect to the guiding device, thereby providing information which enables a surgeon to position the treatment tool at a selected distance and position with respect to the guiding element.

In a variety of preferred embodiment described in detail below, the guiding element is mounted within a catheter, which catheter is used to deliver the guiding element to a reference site, which reference site is a selected site within a body conduit.

In the following, a variety of apparatus and methods are presented, which serve to direct a treatment tool to a locus defined with reference to a guiding element placed at a reference site, thereby delivering that treatment tool to a treatment site which a surgeon desires to treat.

Figure 1:
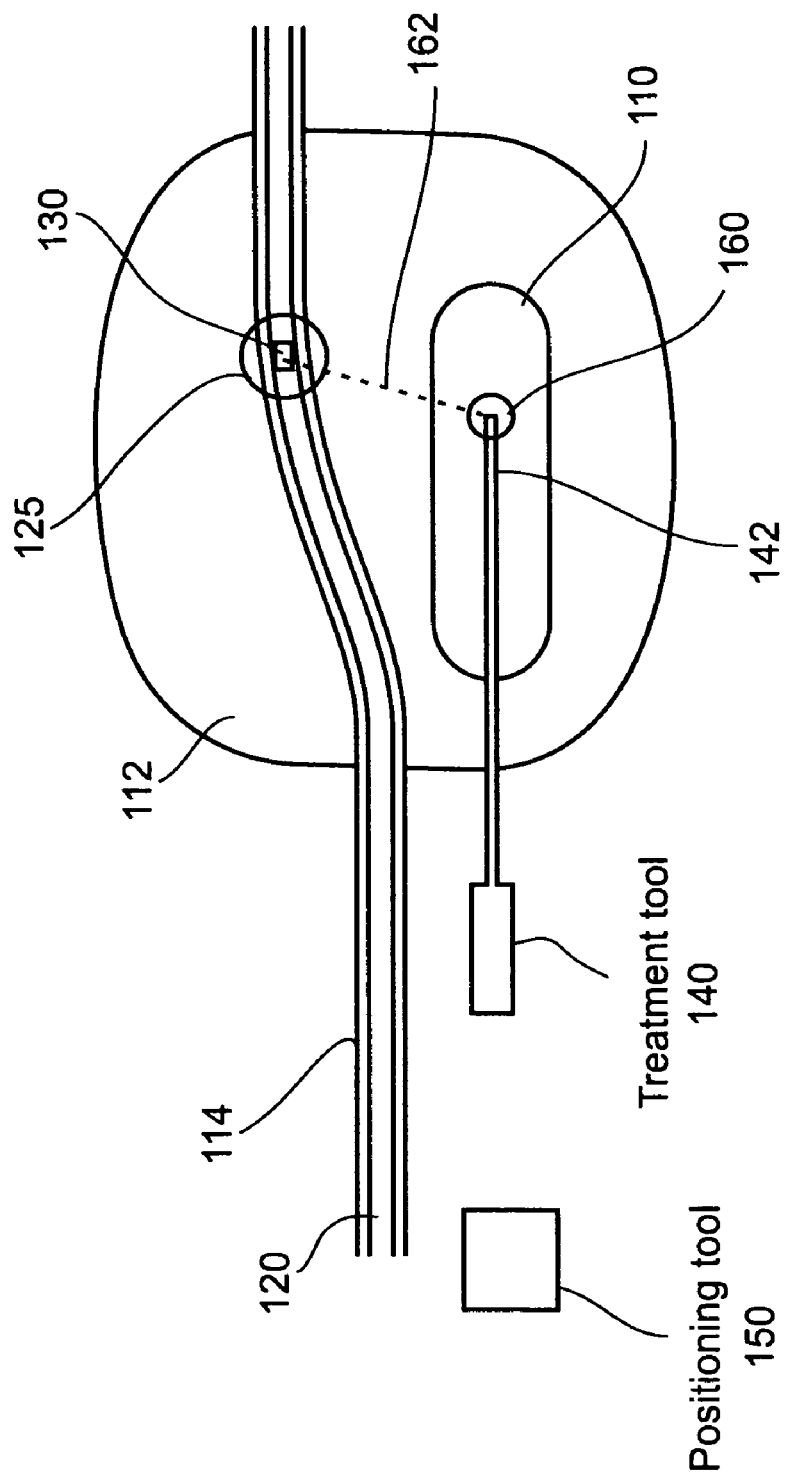

Attention is now drawn to FIG. 1, which is a simplified schematic of an apparatus for delivering a treatment tool to a treatment site, according to an embodiment of the present invention. FIG. 1 presents an organ 112 having a treatment site 110, such as a tumor or other pathological tissue, which a surgeon desires to treat. A selected portion of a body conduit 114 passing in proximity to treatment site 110 is selected as a reference site 125, and a catheter 120 is passed through conduit 114. Reference site 125 is a site having a known spatial relationship to treatment site 110, which spatial relationship may have been ascertained by inspection of images obtained, prior to the operation, through use of various well-known imaging modalities. The known spatial relationship between reference site and treatment site may also be obtained from a priori knowledge, e.g., of well-known anatomical structures.

A guiding element 130, or alternatively a plurality of guiding elements 130, mounted on or within catheter 120, is caused to advance within conduit 114 until guiding element 130 is positioned at reference site 125. Thus positioned, guiding element 130 has a known spatial relationship with treatment site 110. Imaging modalities or various other means, some of which are mentioned in the following, may be used to accurately position guiding element 130 at reference site 125.

Alternatively, guiding element 130 may be caused to move through conduit 114 until positioned at some proximity to treatment site 110, at which time imaging modalities or other means may be utilized to determine the exact position of guiding element 130, and the thus determined position of guiding element 130 is then designated as reference site 125.

In other words, either an optimal reference site 125 is selected and guiding element 130 is maneuvered to that site 125, or alternatively an approximate reference site is selected, guiding element 130 is maneuvered into that approximate position, and imaging modalities or other means are used to determine the position of guiding element 130, which is thereafter considered to be reference site 125. In either case, reference site 125 has a known spatial relationship to desired treatment site 110, and guiding element 130 is positioned at reference site 125.

A positioning tool 150 may then be used to guide a treatment tool 140, optionally having a distal treatment head 142, towards and into a target locus 160 having a selected positional relationship 162 with guiding element 130, thereby positioning treatment head 142 of treatment tool 140 at treatment site 110.

Alternatively, if treatment tool 140 has been positioned by other means within the body of a patient, positioning tool 150 may be used to confirm that treatment head 142 of treatment tool 140 is correctly positioned at treatment site 110.

In a preferred procedure, a surgeon selects as reference site 125 a selected portion of a natural body conduit. A surgeon's knowledge of the body's natural conduit system (including lymphatic & blood vessels, arteries, veins, respiratory tracts & breathing system, gastro-intestinal tracts, urethral tracts etc.) permits him to select as reference site an easily reached part of the body whose anatomy is well understood. The spatial relationship between a selected reference site and a desired treatment site may be ascertained based on generally known physiology, and based on statistical studies of patient physiologies. Alternatively or additionally, the spatial relationship between reference site 125 and treatment site 110 pertaining in a particular patient's case may be ascertained based on studies of that patient's specific pathology, determination being made according to studies based on imaging modalities such as ultrasound, x-ray, MRI, CT, utilized prior to the surgical procedure. Alternatively or additionally, knowledge of the spatial relationship between the selected reference site and the desired treatment site may be further ascertained based on physiological information gleaned and/or physiological measurements made during the course of a surgical procedure.

Reference site 125 is preferably a selected portion of a naturally occurring body conduit such as conduit 114. Consequently, it is generally possible to introduce guiding element 130 into that body conduit 114, and to advance guiding element 130 along conduit 114 to a position selected as reference site 125 for the operation. In a preferred embodiment conduit 114 is accessible through the body's natural entrances, such as the mouth, the urethra, or the rectum. Alternatively, conduit 114 may be accessible through a percutaneous intervention giving access to the blood vessel system, or via endoscopic or limited open surgery.

In a recommended procedure, a surgeon will select as reference site a portion of an accessible conduit 114 that is in proximity to a desired treatment site 110. Preferably, a selected conduit 114 will have a well-understood spatial relationship to desired treatment site 110. For example, in treatment of Benign Prostate Hyperplasia ("BPH"), a well-chosen conduit 114 would be the urethra, since the urethra is accessible through an existing natural opening in the body, and passes within an enlarged prostate whose volume is to be reduced in a surgical procedure. In this example, an appropriate reference site would be a segment of the urethra located within the prostate. It is recommended that, for various reasons of familiarity and efficiency, a surgeon will select a consistently defined reference site for each performance of a particular type of surgical procedure. Thus, selection of a defined portion of a urethra passing through a prostate as reference site 125 might be standard procedure for treatment of BPH, according to a preferred embodiment of the present invention.

Although, for each patient, knowledge of the spatial relationship pertaining between a selected reference site and a desired treatment site may be gleaned from standard imaging modalities such as x-ray and fluoroscope, ultrasound, MRI, and CT, reasonably accurate spatial information may in many cases also be derived from generally known physical characteristics of human anatomical systems and their well-known pathologies. For example, in treating BPH, once a diagnosis is established, basic information about the size and location of volumes to be ablated may easily be defined in terms of the spatial relationship between those volumes to be ablated, and the position of a segment of the urethra passing through the prostate.

Figure 2A:
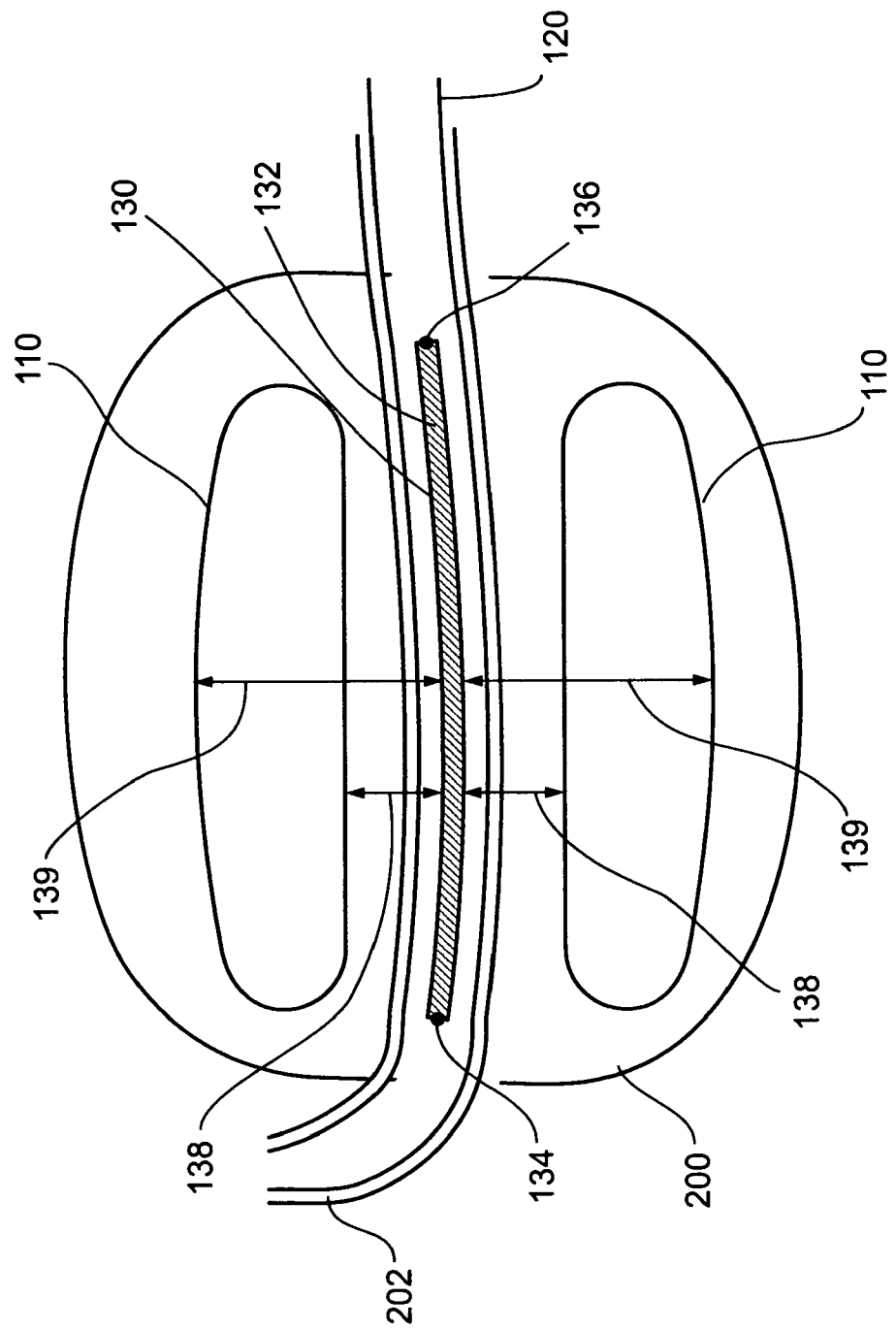

Attention is now drawn to FIG. 2A, which is a simplified schematic of a prostate requiring treatment for BPH, showing an elongated guiding element, according to an embodiment of the present invention.

FIG. 2A presents an enlarged prostate 200 traversed by a urethra 202. A catheter 120 is passed through urethra 202. Catheter 120 comprises a guiding element 130. In the following, a guiding element 130 of shaped to be long and narrow will be termed a guiding segment 132. Guiding segment 132 extends between guiding segment proximal point 134 and guiding segment distal point 136. In treatment for BHP, a recommended length for guiding segment 132 is between 0.5 cm and 8 cm, and most preferably about 2-5 cm. Optimal guiding segment length for a particular patient can be measured using a cystoscope, and placement of guiding segment 132 centered within the prostate portion of the urethra can be easily accomplished based on cystoscopic measurements of distances from the penis urethra entrance to the entrance and exit points of the portion of the urethra which passes through the prostate. Location of the distal exit of the urethra from within the prostate can also accurately be measured by inserting a balloon catheter into the bladder, inflating the balloon, and pulling the catheter backwards until its movement is blocked by the inflated balloon encountering the entrance of the urethra into the bladder.

FIG. 2A presents a case in which it is possible to predetermine a target site for treatment, a reference site, and a spatial relationship between the two, with predetermination being based on generally known physiological data, including statistically established probabilities of various physical relationships, and further based on typical treatment scenarios, and further based on known patient-specific information. Thus, in a relatively simple example of treatment of BPH (presented in further detail below), where the goal of the operation is to ablate tissue contained within the prostate and not extending beyond the boundaries of the prostate, to avoid damage to anus, nerves, blood vessels and other organs external to the prostate, while also avoiding ablation of tissue close to the urethra, to avoid damage to the urethra, a treatment site definition 110 may be predetermined, in the abstract, as a volume of points whose distance from the urethra is greater than a selected minimum distance 138, and less than a selected maximum distance 139, from a selected section of the prostatic urethra. Thus, in treatment for BHP and in similar embodiments of the present invention, selection of treatment site and reference site, and determination of the appropriate distance between the two, may be largely or entirely based on knowledge of the anatomic structure of the organ and of the effective range of influence of a selected therapeutic surgical tool.

For example, in the treatment of BPH the defined treatment site may be simply a hollow cylinder having a constant parallel distance from guiding segment 132, along its length. Such an operation is facilitated by use of a urethral catheter having straightening features used to straighten the urethra, thereby much simplifying the organ geometry and facilitating use of parallel insertion of ablation needles, in parallel to the direction of the urethra and at a predetermined distance therefrom, as a treatment method. Examples of catheters having such straightening features are presented hereinbelow.

Alternatively, a treatment locus may have any other shape or orientation, so long as its placement and orientation with respect to the guiding segment is known.

Attention is now drawn to FIG. 2B, which is a simplified schematic of a prostate requiring treatment for BPH, showing an elongated guiding element and a positioning device, according to an embodiment of the present invention.

FIG. 2B presents an enlarged prostate 200 requiring treatment for BPH. In addition to features common to FIGS. 2A and 2B, FIG. 2B presents a positioning tool 150, operable to position a treatment tool 140 with respect to a treatment site 110. As may be seen in greater detail in FIGS. 3-8, positioning tool 150 may be embodied as a template 230 formed with a set of apertures 240 sized and shaped to permit passage of one or more treatment tools 140. Apertures 240 are such as to orient treatment tools 140 passed therethrough in determined directions. In a currently preferred embodiment, all treatment tools 140 passed through an aperture 240 of template 230 are directed in parallel, and are held perpendicular to template 230.

Utilization of template 230 is shown in greater detail in FIGS. 3-8.

Figure 3:
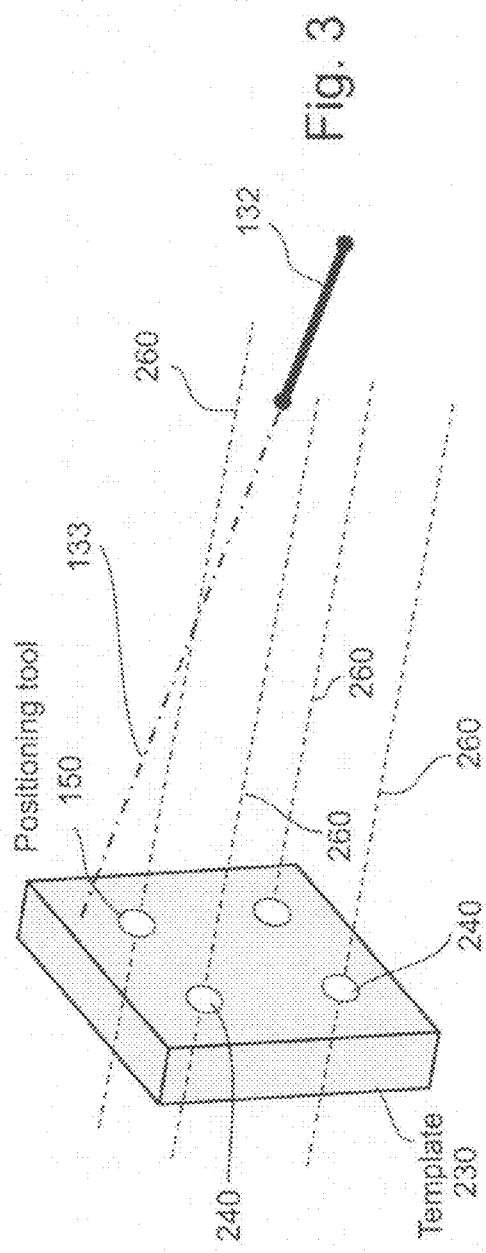

Attention is now drawn to FIG. 3, which presents a positioning tool 150 embodied as a template 230, according to an embodiment of the present invention. Directional lines 260 indicate the direction of orientation which will be imposed on any treatment tool 140 (not shown) passed through an aperture 240 of template 230. Guiding segment 132 is shown in a random orientation with respect to template 230, as shown by guiding segment directional line 133. For simplicity of exposition catheter 120 on which guiding section 132 is mounted is not shown in FIGS. 3-8.

Attention is now drawn to FIGS. 4 and 5, which represent steps in a process of aligning guiding segment 132 and template 230 with respect to each other, according to an embodiment of the present invention. FIG. 4 shows a guiding segment directional line 133, representing the orientation of guiding segment 132. In FIG. 4 template 230 is reoriented with respect to guiding segment 132 in such a way that guiding segment directional line 133 points to the center of template 230. In FIG. 5 template 230 is reoriented with respect to guiding segment 132 in such a way that guiding segment directional line 133 is perpendicular to template 230. The steps shown in FIGS. 4 and 5 may be undertaken in either order, or simultaneously. FIGS. 4 and 5 illustrate a process by which template 230 is oriented with respect to guiding segment 132 in such a way that guiding segment directional line 133, extending the direction of guiding segment 132, when guiding segment 132 is installed in a selected reference site such as in the prostatic urethra, is so oriented as to intersect substantially near the center of template 230, and is substantially perpendicular thereto.

Attention is now drawn to FIG. 6, which presents a treatment tool passed through an aperture of a template oriented with respect to a guiding segment installed at a reference site, according to an embodiment of the present invention.

FIG. 6 presents a treatment tool 140 having a distal treatment head 142, introduced through an aperture 240 of template 230. Guiding segment 132 has been centered with template 230 and been made perpendicular to template 230, as shown in FIGS. 4 and 5. Treatment tool 140 is forced to be perpendicular to template 230 by virtue of the form of apertures 240, which are designed and constructed for this purpose. Thus, consequently, treatment tool 140 is held necessarily substantially parallel to guiding segment 132.

Attention is now drawn to FIG. 7, which presents a plurality of treatment tools held parallel to guiding segment 132, according to an embodiment of the present invention. In FIG. 7 each treatment tool 140 is shown surrounded by an ablation volume 144, that is, a volume of tissue whose ablation is assured by activation of each respective treatment tool 140.

Attention is now drawn to FIG. 8, which presents the configuration shown in FIG. 7, as seen from an "end-on" perspective. It may be seen from FIG. 8 that ablation volumes 144 surround or partially surround, but do not intersect with, guiding element 132. Note also that, as shown in FIGS. 2A and 2B, guiding element 132 is placed within prostatic urethra 202, consequently the ablated volume of tissue surrounds, but does not include, prostatic urethra 202. As noted above, the operation depicted in FIGS. 7 and 8 is facilitated by use of a stiffening element accompanying guiding segment 132, which assures that the portion of prostatic urethra defined as reference site 125 is substantially straight.

Note further distance "L" as it appears in FIGS. 2B, 6, 7, and 8. Distance "L" is the straight-line distance from template 230 to guiding segment proximal point 134 as shown in FIG. 2B. If active treatment heads 142 of treatment tools 140 extend in length approximately the distance between guiding segment proximal point 134 and guiding segment distal point 136, and if treatment tools 140 are extended through template 230 to a distance such that the proximal limit of their active treatment heads 142 extends beyond template 130 at a distance substantially equal to distance "L", then the ablation volume created by activation of treatment tools 130 as shown in FIGS. 7 and 8 will result in an ablation volume which substantially surrounds guiding segment 132, and which has proximal and distal extremes substantially equidistant from template 132, at a distance corresponding to the proximal and distal extreme points of guiding segment 132.

Note further that, if guiding segment 132 is placed within prostatic urethra 202 and does not extend beyond the proximal and distal extremes of prostate 200, then ablation volumes 144, as shown by FIGS. 7 and 8, will be contained within prostate 200. Ablation of ablation volumes 144 as shown will ablate prostate tissues, as required for treatment of BPH, yet will harm neither the prostatic urethra nor the nerve bundles, bladder, anus, nor other structures which are proximate to prostate 200.

Thus, FIGS. 2B-8 illustrate a device and method whereby a surgeon may successfully ablate prostate tissue to treat BPH, without requiring use of imaging modalities during an ablation procedure.

To summarize the procedure as outlined in FIG. 2B-8, a surgeon places a catheter which comprises a guiding segment within a prostatic urethra (which constitutes a reference site), orients template 230 so as to centered on and perpendicular to that guiding segment, then uses template 230 to guide one or more treatment tools 140 to an appropriate position and depth, at a selected distance from guiding segment 132. Having thus guided treatment tools 140 to that defined locus, the surgeon may used treatment tools 140 to treat tissues at that locus, confident, without need of direct observation, that those treatment tools 140 are indeed positioned at a desirable, and expected, treatment site.

It is to be noted that although the discussion of FIGS. 2A-8 related particularly to treatment of BPH, the apparatus and method presented hereinabove are applicable to a wide variety of treatment applications. In particular, a reference site other than the prostatic urethra may be used, and treatment sites may be identified according to any manner of accepted medical practice, for example by inspection of images created by any one of a variety of imaging modalities.

As noted, it is a requirement of the method presented by FIGS. 2B-8 that template 230 be appropriately oriented with respect to guiding segment 132. Various techniques and devices for orienting template 230 with respect to guiding segment 132 will be presented in the following.

It is noted that alternate constructions of template 230 are possible. In particular, so long as some mechanism is provided to relate the distance and angular direction from a template surface to a guiding element installed at a reference site to the distance and angular direction from that template surface to a treatment site, the essential functionality of template 230 is preserved.

Attention is now drawn to FIG. 9, which presents a simplified schematic of an alternative construction of a positioning tool 150, according to an embodiment of the present invention. An orientation tool 260 comprises two or more arms 262A and 262B, at least some of which are preferable of variable length, arms 262A and 262B forming a variable angle between them. Angular gradations 264 are provided for measuring the variable angle between arms 262A and 262B, and length gradations 266 are provided for indicating a selected variable length setting for at least one of the arms. It will be clear to one skilled in that art that orientation tool 260 may be used in a manner similar to template 230, to deliver a distal treatment head 142 of a treatment tool 140 to a treatment site 110, given a known distance of a guiding element 130 from orientation tool 260, and a known spatial relationship between guiding element 130 and selected treatment site 110. Simple trigonometric functions will provide answers as to the appropriate orientation of orientation tool 260, a desired angle between arms 262, and an appropriate length and for extending treatment tool 140. Thus, placing guiding element 130 at reference site 125, and knowing a (predetermined or observed) spatial relationship between reference site 125 and treatment site 110, orientation tool 260 may first be lined up so that arm 262A points toward guiding element 130, then trigonometric functions used to determine a required angular setting of the angle between arms 262, and to determine an appropriate length setting for arm 262B. Placing a treatment tool 140 in arm 262B, setting the desired angular setting between arms 262, and then advancing treatment tool 140 by gradually extending arm 262B until the calculated depth is reached, will have the effect of delivering distal treatment head 142 of treatment tool 140 to treatment site 110.

In FIG. 9, arms 262 are presented as simple mechanical arms, and simple visual gradations 264 and 266 are provided to enable measurements of angle and of length. It will be clear to one skilled in the art that alternative constructions are possible, including use of an electro-mechanical or electronic angular measurement tool 284, an electro-mechanical or electronic length measurement tool 288, an automatic or semiautomatic controller 190 for executing trigonometric calculations, and a servo-motor system 192, optionally controllable by controller 190, to modify the angular separation of arms 262 and to individually shorten or lengthen arms 262, as required, according to trigonometric calculations, to deliver treatment tool 140 to treatment site 110.

Attention is now drawn to FIGS. 10-21, which present further details of devices and methods for orienting template 230 with respect to guiding segment 132. As mentioned hereinabove, operation of the apparatus described in FIGS. 2B-8 and of the apparatus described in FIG. 9 requires that a template 230 or other positioning tool 150 be oriented so as to have a know orientation (preferably, centered and perpendicular, as shown in FIGS. 4 and 5) with respect to guiding element 130. Yet, guiding element 130 is typically installed at a site inside the body, and is not directly visible to an operator. FIGS. 10-21 provide various devices and methods for orienting template 230 with respect to guiding element 130, which devices and methods do not require use of imaging modalities for their operation.

Attention is drawn to FIG. 10, which presents a simplified schematic of a multi-joint locking catheter 250, according to an embodiment of the present invention. Multi-joint locking catheter 250, which comprises a guiding element 130 formed as an extended guiding segment 132, further comprises lockable joints 260A and 260B.

FIG. 10 represents a first stage in the use of catheter 250. During this first stage, joints 260A and 260B are free to move arbitrarily. Distal end 252 of catheter 250 is moveable as well. The resulting freedom of movement of the various parts of catheter 250 facilitates insertion of catheter 250 into a patient's urethra or into a similar body conduit. Flexibility of catheter 250 enables it to conform to the body's geometry during insertion.

Attention is now drawn to FIG. 11, which represents a second stage in use of multi-joint locking catheter 250, according to an embodiment of the present invention. Rigidity and deterministic geometry are achieved by locking joints 260A and 260B, and by connecting catheter 250 to template 230, at connecting joint 270.

Attention is now drawn to FIG. 12, which represents a third stage in use of multi-joint locking catheter 250, according to an embodiment of the present invention. Catheter 250 is now shown as connected to template 230, but template 230 is not yet aligned perpendicularly to guiding segment 130. Perpendicular alignment is the desired state, as shown and described hereinabove in the context of the discussion of FIG. 5.

To achieve perpendicular alignment, guiding segment 132 is embodied as an electromagnetic field generator 280, powered from either an external or an internal energy source (not shown). An electronic field sensor 290, preferably mounted on template 230, is capable of detecting an electromagnetic field generated by field generator 280. As shown in FIG. 12, non-perpendicular orientation of template 230 with respect to field generator 280 (which is guiding segment 132), is detectable as a component vector 291 of the detected field sensed by sensor 290.

Attention is now drawn to FIG. 13, which represents a fourth stage in use of multi-joint locking catheter 250, according to an embodiment of the present invention. FIG. 13 differs from FIG. 12 in that template 230 has been rotated around joint 270 until detected component 291 of the field signal detected by sensor 290 disappears. Disappearance of component 291 of the detected signal indicates that sensor 290, and with it template 230, are perpendicular to field generator 280 embodied in guiding segment 132. At this point joint 270 can be locked in place, and template 230 is fixed in perpendicular orientation to guiding segment 132, as required for use of the device and method as generally described hereinabove in FIGS. 2B-8.

Attention is now drawn to FIG. 14, which presents an alternative configuration for achieving perpendicular orientation of template 230 with respect to guiding segment 132, according to an embodiment of the present invention.

The alternative configuration presented by FIG. 14 is mechanical in nature; it requires no electronic components. As will be clear from inspection of FIG. 14, angles $\alpha$, $\beta$, and $\delta$ determine the angle of template 230 with respect to the orientation of guiding segment 132. If the sum of $\alpha$, $\beta$, and $\delta$ is 90°, then template 230 is perpendicular to guiding segment 132, and treatment tools passed through guiding apertures 240 of template 230 will be parallel to guiding segment 132. Locking joints 262A, 262B, and 270 into a configuration whose sum is 90° can be achieved in various ways. The simplest manner of ensuring that joints 262A, 262B, and 270 will lock only into the required 90°-sum configuration is to enable each joint to lock only into a single angle, choosing of course angles whose sum is 90°. Alternative constructions include that of allowing the above-named joints each to lock in a plurality of possible positions, providing a visible indication of each selected position, and depending on an operator to select an appropriate combination of joint locking angles. Yet another possible configuration is to allow two of the joints to lock in multiple or indeed in random positions, to provide those joints with sensors 292 and 294 able to report their positions to a controller 290, and to provide a third joint (e.g., joint 270) with a servo-motor 296, controllable by controller 290, and which automatically positions joint 270 at an angle which brings the sum of angles $\alpha$, $\beta$, and $\delta$ to 90°.

Attention is now drawn to FIG. 15, which presents yet another configuration for orienting a template 230 with respect to a guiding element 130, according to an additional embodiment of the present invention.

The configuration presented by FIG. 15 requires no physical contact between catheter 120, containing guiding element 130, and template 230. If FIG. 15 is compared to FIG. 13 it may be seen that joints 270, 262A, and 262B are absent.

In the configuration shown in FIG. 15 an adjustable base 310 is provided to support template 230 and to optionally lock template 230 in a selected position. In this embodiment, a plurality of sensors 290 (preferably four sensors, as will be shown hereinbelow in FIG. 16) are mounted on template 230, and serve to enable an operator to orient template 230 to be centered and perpendicular to guiding segment 132, without requiring a physical connection between template 230 and catheter 120.

Attention is now drawn to FIGS. 16A and 16B, which provide simplified additional views of template 230, showing sensors 290A, 290B, 290C, and 290D mounted thereon, according to an embodiment of the present invention.

With reference to the embodiment presented by FIGS. 15, 16A and 16B, in a preferred mode of operation, alignment of template 230 proceeds in two steps.

First, template 230 is rendered perpendicular to guiding segment 132 using the techniques presented hereinabove with reference to FIGS. 12 and 13. Guiding segment 132 comprises a field generator 280 operable to create an electromagnetic field detectable by sensors 290 mounted on template 230. FIG. 15 shows that when template 230 is not perpendicular to guiding segment 312, a vector component 291 can be found in electromagnetic signals detected by sensors 290. Template 230 can be turned on various axes until component 291 of the field signals detected by sensors 290 disappears. Disappearance of component 291 of the detected signal indicates that sensors 290, and with them template 230, are perpendicular to field generator 280, hence perpendicular to guiding segment 132.

Referring now to FIG. 16A, at the stage of the process presented in FIG. 16A, template 230 has been rendered perpendicular to guiding segment 132, as shown in FIG. 5, but has not yet been centered with respected to guiding segment 132, as shown in FIG. 4.

Mark 320 indicates the point at which a line extending in the direction in which guiding segment 132 is oriented (that is, a line equivalent to guiding segment directional line 133 of FIGS. 3-5) would intersect template 230. As shown in FIG. 16A, when template 230 is perpendicular to the direction of guiding segment 132, and field generator 280 radiates an electromagnetic signal, strength of that signal as detected by the various detectors 290 is a function of each detector's distance from point 320. Thus, in FIG. 16A, detectors 290A and 290B detect strong signals (as shown by arrows 330A and 330B), whereas detectors 290C and 290D detect relatively weaker signals, as indicated by arrows 330C and 330D. In contrast, when template 230 is centered with respect to guiding element 132, as shown in FIG. 16B, so that point 320 is equidistant from each of sensors 290, detected signal strength of a field generated by generator 280 is equally strong at each of sensors 290, as is shown in the figure by the equal lengths of arrows 332A, 332B, 332C, and 332D. Thus, a second step required to complete alignment of template 230 with guiding segment 132, according to the embodiment presented by FIGS. 15, 16A and 16B, is simply to move template 230 in its own plane (template 230 being already perpendicular to guiding segment 132 as result of minimizing vector components 291 of signals detected by sensors 290), until equal signal strengths are detected at each of sensors 290.

It is noted that the process here described is one of tilting and sliding template 230 in response to received electromagnetic signals. It will be clear to one skilled in the art that addition of a control unit 336 operable to receive signal information from sensors 290, to calculate an appropriate response, and to send commands to one or more servo motors 340 operable to title and to slide template 230, will serve to automate the process here described.

Attention is now drawn to FIG. 17, which presents a side view of the detatched-template configuration of FIGS. 15, 16A, and 16B, with template 230 perpendicular to, and centered with respect to, guiding section 132. As discussed above, field generator 280 generates an electromagnetic signal from within guiding segment 132, which signal is detected by sensors 290. Equal signal strength is detected at each detector 290 when template 230 is properly aligned as previously explained. Under these circumstances, distance "L" may be calculated as a function of detected signal strength at sensors 290, since the closer field generator 280 is to sensors 290, the stronger their detected signal will be.

Attention is now drawn to FIG. 18, which is a simplified schematic of a flexible self-stiffening catheter during insertion into a urethra of a prostate, according to a further embodiment of the present invention.

In FIG. 18, a flexible self-stiffening catheter 350 having a proximal connection point 352 is design to be attachable to a template 230 or to any other form of positioning tool 150. Initially flexible, catheter 350 can easily be inserted into a urethra and advanced towards and into a prostatic portion of a urethra.

Attention is now drawn to FIG. 19, which is a simplified schematic of catheter 350 in stiffened state. A pressurized fluid source 360 supplies a pressurized fluid 362 (gas or liquid) to an inflation lumen 364 running the length of catheter 350. The walls of lumen 364 are preferably constructed of a material, such as thin metal or low compliance nylon, which assumes a pre-determined geometry when inflated. Inflating lumen 364 thus forces catheter 350 into a shape which conforms to a pre-determined geometry, which geometry includes a straight section 370 designed to fit within a prostatic urethra, and an external section 372 whose pre-determined geometry is designed to facilitate utilization of catheter 350 with template 230, as generally described hereinabove, or with another form of positioning device 150.

Straight section 370 incorporates a guiding element 130. It is also noted that inflation of inflation lumen 364 forces section 370 to be straight, which forces the prostatic portion of the urethra to be straight, thereby greatly facilitating treatment of tissues surrounding that prostatic urethra.

Thus, a first effect of inflating inflation lumen 364 is to force a prostatic urethra, into which straight section 370 has been placed, into a straight linear orientation, thereby creating a desirable arrangement wherein that prostatic urethra is both straightened and in a known position. A second effect of inflating inflation lumen 364 is to force external section 372 into a pre-defined geometry which enables to calculate distance "L" and brings connection point 352 into a known sidewise displacement from the position and direction of straight section 370. Fastening connecting point 352 to an appropriate joint a template 230 (not shown), at an appropriate known angle, then enables use of that template 230 to guide a plurality of treatment tools 140 (not shown) to desired loci alongside straight section 370 and at a pre-planned distance therefrom, for treatment of BPH, as has been described hereinabove.

Attention is now drawn to FIGS. 20 and 21, which present, in simplified schematic, two views of a flexible catheter having an insertable stiffening element, according to a further embodiment of the present invention.

As shown in FIG. 20, a flexible stiffenable catheter 390 comprises an external sheath 392 having a stiffener lumen 394, and a stiffener 396 insertable into stiffener lumen 394. The shape, purpose, and function of catheter 390 is identical to that of catheter 350 described hereinabove, with the difference that whereas catheter 350 is stiffened by inflation with a fluid, catheter 390 is stiffened, once catheter 390 has been appropriately inserted into a prostatic urethra, by insertion of stiffener 396 into lumen 394, thereby straightening the prostatic urethra and bringing catheter 390 into a known pre-determined geometry, thereby permitting use of catheter 390 for guiding placement of a treatment tool to a treatment site, as described hereinabove.

Stiffener 396 is of rigid or semi-rigid construction, is of a known pre-determined shape, and, in a currently preferred construction, is hollow.

Attention is now drawn to FIG. 21, which presents a simplified schematic view of catheter 390 in stiffened configuration, with stiffener 396 inserted into lumen 394.

Attention is now drawn to FIG. 22, which presents a simplified schematic of a treatment tool positioning apparatus, according to a further embodiment of the present invention.

In FIG. 22, treatment tool positioning apparatus 400 comprises a base 402 connected to a jointed arm 410 having a plurality of freely moving joints, represented in FIG. 22 as joints 420A and 420B, and a guiding element 130, which may be formed as an elongated guiding segment 132. Guiding segment 132 may itself include one or more moveable joints 420, designated 420A, 420B, etc.

Each joint 420 comprises a position sensor 430, designated 430A, 430B, etc. Each position sensor 430 is capable of sensing the angular position of its associated joint, and of reporting the detected angles electronically, either by wire or by wireless digital transmission, to a controller 440. Joint 415, linking arm 410 to base 402, is similarly equipped with a position sensor 418, similarly capable of reporting the angular position of joint 415.

Sensors 415 and 420 might, for example, be a variable resistances whose resistance to electric current is dependent on the angle of the joint. Alternatively, these sensors might be digital devices intermittently reporting their positions over a digital data line or a wireless link.

Given known lengths of arm segments between each joint, simple trigonometry may be used to calculate position and orientation of guiding element 130 with respect to base 402. This calculation is preferably carried out automatically by controller 440.

Given a known position of guiding element 130 relative to base 402, and a known position of a treatment site 110 relative to guiding element 130, one may easily calculate the position of treatment site 110 with respect to base 402. Knowing the position of treatment site 110 with respect to base 402, an operator, utilizing various methods well known in the art, may easily guide an independently moveable treatment tool 460 to treatment site 110, where it may be used to diagnose or to treat body tissue. Treatment tool 460 may be implemented, for example, as a standard industrial robotic arm 470 controlled by controller 440, and having an extensible therapeutic head 472 adapted to percutaneous introduction into the body of a patient.

Attention is now drawn to FIG. 23, which is a simplified schematic of a treatment tool positioning apparatus 500 incorporating an energy transmitter and an energy detector, according to a preferred embodiment of the present invention.

Apparatus 500 comprises a transmitting catheter 505 suitable to be inserted in the urethra of a patient. Catheter 505 incorporates a guiding element 130 comprising a transmitter 510, and preferably comprising a urethra straightening device 512 for straightening the prostatic portion of a urethra. Straightening device 512 may be a rigid section of catheter 505, or a section switchable between flexible and rigid configuration, such as a section utilizing techniques presented hereinabove with reference to FIGS. 18-21.

Transmitter 510 may be a transmitter of electromagnetic energy 514, a transmitter of acoustic energy 516, or a transmitter of any other kind.

Apparatus 500 further comprises one or more treatment tools 520. Treatment tool 520 comprises a distal portion 522. Distal portion 522 of treatment tool 520 comprises a therapeutic element 530, and a signal detection sensor 540. Therapeutic element 530 is an element operable to produce a therapeutic or diagnostic effect, such as ablation or a short-range imaging. Signal detection sensor 540 is a sensor operable to detect a signal generated by transmitter 510. Changes in spatial distance between transmitter 510 and sensor 540 are detectable as a change in signal strength, or in signal phase, or in the time required for a signal to travel between transmitter 510 and sensor 540. Thus, after calibration, the described transmitter-sensor combination can be used to determine and report absolute distance between transmitter 510 and sensor 540, which is to say, between guiding element 130 which comprises transmitter 510, and therapeutic element 530 of treatment tool 520, which is adjacent to, or co-located with, sensor 540. Transmitter 510 and signal sensor 540 comprise internal or external power sources (not shown). Output from signal sensor 540 may be fed to a display system 542 useful to guide a surgeon in manipulating and placing treatment tool 520, or may be fed to a controller 544 operable to calculate movements required to deliver treatment tool 520 to a treatment site, and to provide commands to servo motors 546 operable to move treatment tool 520 according to those commands. Display system 542 may comprise a computerized system for signal analysis and for display enhancement under algorithmic control.

Note that in an alternative construction, the positions of transmitter 510 and sensor 540 may be reversed, with transmitter 510 incorporated in treatment tool 520, and sensor 540 incorporated in guiding element 130.

Attention is now drawn to FIG. 24, which is a simplified schematic of a treatment tool positioning apparatus 600 incorporating an energy transmitter co-located with an energy sensor, according to an additional preferred embodiment of the present invention.

Apparatus 600 comprises a transmitting and receiving catheter 605 suitable to be inserted in the urethra of a patient. Catheter 605 preferably comprises a urethra straightening device 612 for straightening the prostatic portion of a urethra. Straightening device 612 may be a rigid section of catheter 605, or a section switchable between flexible and rigid configuration, such as a section utilizing techniques presented hereinabove with reference to FIGS. 18-21.

Catheter 605 incorporates a guiding element 130 comprising a transmitter 610 and a sensor 640.

Transmitter 610 may be a transmitter of electromagnetic energy 614, a transmitter of acoustic energy 616, or any other transmitter.

Apparatus 600 further comprises one or more treatment tools 620. Treatment tool 620 comprises a distal portion 622 incorporating a therapeutic element 630 operable to produce a therapeutic or diagnostic effect, such as ablation or short-range imaging. Distal portion 622 of treatment tool 620 is designed and constructed so as to reflect energy transmitted by transmitter 610.

Signal detection sensor 640 is a sensor operable to detect signals generated by transmitter 610 and reflected from distal portion 622 of treatment tool 620. Changes in spatial distance between transmitter 610 and distal portion 622 are detectable as changes in signal strength, or in signal phase, or in time required for a transmitted signal to travel between transmitter 610 and distal portion 622, to be reflected from distal portion 622, and to travel back to sensor 640.

Thus, after calibration, the transmitter-sensor combination of apparatus 600 can be used to determine and report absolute distance between transmitter 610, mounted within guiding element 130, and a distal portion 622 of a treatment tool 620 that reflects signals transmitted by transmitter 610.

Transmitter 610 and signal sensor 640 comprise internal or external power sources (not shown). Output from signal sensor 640 may be fed to a display system 642 useful to guide a surgeon in manipulating and placing treatment tool 620, or may be fed to a controller 644 operable to calculate movements required to deliver treatment tool 620 to a treatment site, and to provide commands to servo motors 646 operable to move treatment tool 620 according to those commands. Display system 642 may comprise a computerized system for signal analysis and for display enhancement under algorithmic control.

Attention is now drawn to FIG. 25, which is a simplified schematic of a treatment tool positioning apparatus 700 operable in conjunction with a conventional imaging device, according to an additional preferred embodiment of the present invention.

Apparatus 700 comprises a catheter 705 suitable to be inserted in the urethra of a patient. Catheter 705 preferably comprises a urethra straightening device 712 for straightening the prostatic portion of a urethra. Straightening device 712 may be a rigid section of catheter 705, or a section switchable between flexible and rigid configuration, such as a section utilizing techniques presented hereinabove with reference to FIGS. 18-21.

Apparatus 700 is designed for use with a conventional imaging device 707, such as an ultrasound imaging system. By way of example, imaging device 707 is represented in FIG. 25 as an ultrasound transducer 709 inserted in an anus of a patient, for imaging a prostate of that patient.

Catheter 705 comprises a guiding element 130, designed and constructed so as to be rendered visible by imaging system 707, and so as to appear distinct from other objects imaged by imaging system 707.

Apparatus 700 further comprises one or more treatment tools 720. Treatment tool 720 comprises a distal portion 722 incorporating a therapeutic element 730 operable to produce a therapeutic or diagnostic effect such as ablation or short-range imaging. Furthermore, distal portion 722 of treatment tool 720 is designed and constructed so as to be visible under imaging system 707, and so as to appear distinct from other objects imaged by imaging system 707.

Thus, guiding element 130 of catheter 705, and distal portion 722 of treatment tool 720, are both distinctively visible under whatever imaging modality is provided by imaging system 707. Imaging system 707 may consequently be used with success to direct placement of treatment tool 720 with respect to the position of guiding element 130. Consequently, when guiding element 130 is placed in a reference site having a known spatial relationship to a desired treatment site, apparatus 700 and imaging system 707 may be used in conjunction to successfully position treatment tool 720 at that desired treatment site. If, for example, guiding element 130 is placed within a straightened portion of a prostatic urethra, imaging system 707 can easily be used to navigate the distal portion of a treatment tool 720 to a locus at a selected distance from that prostatic urethra, e.g., for treatment of BPH.

It is noted that, although many of the embodiments presented in the accompanying Figures and discussed hereinabove were presented in the context of treatment of a prostate, and particularly of treatment of a prostate for BPH, it is to be understood that the example of treatment of a prostate and of a BPH condition are exemplary only, and not to be construed as limiting the scope of the invention.

It is expected that during the life of this patent many relevant devices for positioning a treatment tool at a treatment site will be developed. The scope of the term "treatment tool positioning apparatus" is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for facilitating treatment of prostate tissue, comprising
delivering a treatment tool to a treatment site within a prostate, by:
   a) placing a guiding element at a reference site within a prostatic urethra, said reference site having a known spatial relationship with said treatment site;
   b) generating a signal at one of a group consisting of said guiding element and said treatment tool;
   c) remotely detecting said generated signal; and
   d) utilizing said remotely detected signal to guide delivery of said treatment tool to said treatment site.

2. The method of claim 1, further comprising utilizing said remotely detected signal to orient a positioning tool with respect to said treatment target, and utilizing said positioning tool to guide advancement of said treatment tool toward said treatment target.

3. The method of claim 2, wherein said positioning tool is an electro-mechanical device.

4. The method of claim 2, wherein said positioning tool comprises a template having an aperture sized and shaped to permit passage of said treatment tool.

5. The method of claim 4, wherein said aperture is sized and shaped to orient said treatment tool in a predetermined direction.

6. The method of claim 5, wherein said predetermined direction is perpendicular to said template.

7. The method of claim 4, wherein said template comprises a plurality of apertures, each aperture sized and shaped to permit passage of a treatment tool.

8. The method of claim 4, wherein said guiding element is a guiding segment which is substantially straight and has a length in excess of 1 cm.

9. The method of claim 8, further comprising orienting said template to be perpendicular to a long axis of said guiding segment.

10. The method of claim 2, further comprising ablating tissue near, but not touching, said prostatic urethra, comprising:
   a) utilizing a catheter to introduce into said prostatic urethra a guiding element embodied as a substantially straight guiding segment oriented in a first orientation, said guiding segment comprises a signal transmitter;
   b) providing a template having a plurality of apertures spaced around a central point, and orienting said template so that longitudinal axes of said apertures are parallel to said first orientation by a signal detector attached to said template to detect a signal generated by said signal transmitter, and manipulating said template orientation until an output from said signal detector is minimized, thereby so orienting said template;
   c) moving said template to equalize readings from a plurality of sensors, thereby centering said template with respect to said guiding segment in such a way that a line, in said first orientation, extending from said guiding segment to said template, would intersect said template at said central point;
   d) deploying at least one treatment tool through at least one of said plurality of apertures; and
   e) utilizing said deployed treatment tools to ablate tissue of said prostate, thereby ablating prostate tissue near, but not touching, said prostatic urethra.

11. The method of claim 1, further comprising utilizing a position-reporting device to report information gleaned from said detected signal to a surgeon, thereby enabling said surgeon to appropriately guide said treatment tool towards said treatment target.

12. The method of claim 1, further comprising using a catheter to place said guiding element at said reference site.

13. The method of claim 12, wherein said guiding element is integrated with said catheter.

14. The method of claim 1, wherein said signal is generated by a signal generator comprised in said treatment tool, and said generated signal is detected by a signal detector comprised within said guiding element.

15. The method of claim 14, wherein said natural body conduit is a blood vessel.

16. The method of claim 14, wherein said natural body conduit is a bronchial tube.

17. The method of claim 14, wherein said natural body conduit is an intestine.

18. The method of claim 14, wherein said natural body conduit is a colon.

19. The method of claim 1, wherein said signal is generated by a signal generator comprised within said guiding element and said generated signal is detected by a signal detector comprised within said positioning tool.

20. The method of claim 1, further comprising utilizing said treatment tool to treat tissue at said treatment site.

21. The method of claim 20, further comprising utilizing said treatment tool to ablate prostate tissue.

22. The method of claim 20, wherein said treatment site is a volume of tissue situated less than a selected maximum distance from said guiding element and more than a selected minimum distance from said guiding element.

23. The method of claim 22, wherein said guiding element is a guiding segment having a length in excess of 1 cm.

24. The apparatus of claim 1, further comprising a treatment tool operable to ablate tissue.

25. A method for delivering a treatment tool to a treatment site within the body of a subject, comprising:
   a) using a catheter, which catheter comprises rigid sections joined by joints which are both flexible and lockable, to place a guiding element at a reference site within a prostatic urethra, said reference site having a known spatial relationship to said treatment site;
   b) attaching a template to said catheter and locking said lockable joints; and
   c) utilizing said template to guide a treatment tool towards said treatment site.

26. The method of claim 25, wherein said catheter joints are lockable at a variety of angles, and at least some of said joints comprise a sensor operable to report an angle at which segments adjacent thereto are joined.

27. The method of claim 26, further comprising orienting said template with respect to said guiding segment by attaching said template to said catheter at an angle calculated as a function of a sum of said reported angles of said plurality of variable joints.

28. The method of claim 25, wherein each of said joints locks at a predetermined fixed angle.

29. The method of claim 26, further comprising centering said template with respect to said guiding segment by selecting a template position which equalizes strengths of signals received at a plurality of sensors monitored on said template, which signals originate at a signal transmitter proximate to said guiding segment.

30. An apparatus for delivering a treatment tool to a treatment site within a prostate, comprising:
   a) a guiding element operable to be placed at a reference site within a prostatic urethra, said reference site having a known spatial relationship with said treatment site, said guiding element comprises a signal generator; and
   b) a positioning tool operable to guide insertion of a treatment tool into said prostate, said positioning tool comprises at least one signal detector operable to detect a signal generated by said signal generator.

31. The apparatus of claim 30, wherein said positioning tool is a mechanical device operable to guide said treatment tool to a position at a selected distance from said guiding element.

32. The apparatus of claim 30, wherein said positioning tool is an electro-mechanical device operable to position said treatment tool at a selected distance from said guiding element.

33. The apparatus of claim 30, wherein said positioning tool comprises a position-reporting device operable to report distance and direction from said guiding element to said treatment tool, thereby providing information enabling a surgeon to position said treatment tool at a said second distance from said guiding element and in said direction from said guiding element.

34. The apparatus of claim 30, further comprising a catheter operable to place said guiding element at said reference site.

35. The apparatus of claim 34, wherein said guiding element is integrated with said catheter.

36. The apparatus of claim 34, wherein said catheter is operable to be flexible, and also operable to be stiff.

37. The apparatus of claim 36, wherein said catheter comprises an inflation lumen, and said catheter is operable to be rendered stiff throughout at least a substantial portion of its length by introduction of pressurized fluid into said inflation lumen.

38. The apparatus of claim 36, wherein said catheter is operable to be stiffened by insertion of an insertable stiffening element.

39. The apparatus of claim 34, wherein said guiding element comprises a transmitter.

40. The apparatus of claim 39, wherein said guiding element comprises a sensor operable to detect a signal transmitted by said signal transmitter and reflected from a treatment tool.

41. The apparatus of claim 40, further comprising a display system operable to receive information from said sensor.

42. The apparatus of claim 40, further comprising a controller operable to calculate movements required to deliver said treatment tool to said treatment site, based on information provided by said sensor.

43. The apparatus of claim 39, further comprising a treatment tool which comprises a sensor operable to detect a signal transmitted by said transmitter.

44. The apparatus of claim 34, wherein said guiding element comprises a sensor, and further comprising a treatment tool which comprises a transmitter, said sensor is operable to detect a signal transmitted by said transmitter.

45. The apparatus of claim 44, further comprising a display system operable to receive information from said sensor.

46. The apparatus of claim 44, further comprising a controller operable to calculate movements required to deliver said treatment tool to said treatment site, based on information provided by said sensor.

47. The apparatus of claim 30, wherein said guiding element is a guiding segment having a length in excess of 1 cm.

48. The apparatus of claim 30, wherein said positioning tool comprises a template having an aperture sized and shaped to permit passage of said treatment tool.

49. The apparatus of claim 48, wherein said aperture is sized and shaped to orient said treatment tool in a predetermined direction.

50. The apparatus of claim 49, wherein said predetermined direction is perpendicular to said template.

51. The apparatus of claim 48, wherein said template comprises a plurality of apertures, each aperture sized and shaped to permit passage of a treatment tool.

52. The apparatus of claim 48, wherein said guiding element is a guiding segment which is substantially straight and has a length in excess of 1 cm.

53. The apparatus of claim 52, further comprising orienting means for orienting said template in an orientation perpendicular to a long axis of said guiding segment.

54. The apparatus of claim 48, wherein said guiding element comprises a signal transmitter and said template comprises a signal sensor.

55. The apparatus of claim 54, wherein said signal sensor is operable to report a signal whose strength is a function of an angle of orientation of said template with respect to said guiding segment.

56. The apparatus of claim 55, wherein said signal sensor is operable to report a signal whose strength is at a minimum when said template is perpendicular to said guiding segment.

57. The apparatus of claim 54, further comprising a plurality of sensors operable to receive a signal generated by said signal transmitter.

58. The apparatus of claim 57, wherein said plurality of sensors is operable to report substantially equal signal strengths when said template is both perpendicular to, and centered with respect to, said guiding element.

59. An apparatus for delivering a treatment tool to a treatment site within a prostate, comprising:
a) a catheter which comprises
  i) a distal portion which includes a guiding element formed for insertion into a prostatic urethra; and
  ii) a medial portion which comprises a plurality of rigid sections joined by flexible joints which are lockable into fixed angles;
b) a template which comprises apertures sized and shaped to said treatment tool and to guide advancement of said treatment tool therethrough.

60. The apparatus of claim 59, wherein at least some of said joints comprise sensors operable to report an angle at which segments adjacent thereto are joined.

61. The apparatus of claim 60, further comprising a servomotor operable to orient said template perpendicularly to said guiding segment.

62. The apparatus of claim 61, wherein said servomotor is operable to orient said template with respect to said catheter at an angle calculated as a function of a sum of said reported angles of said plurality of variable joints.

* * * * *